US012653552B2

(12) United States Patent
Trabish et al.

(10) Patent No.: US 12,653,552 B2
(45) Date of Patent: Jun. 16, 2026

(54) KNEE BALANCING SYSTEM USING PATIENT SPECIFIC INSTRUMENTATION

(71) Applicant: Orthosensor Inc., Dania, FL (US)

(72) Inventors: Masei Trabish, Folsom, CA (US); Martin Roche, Fort Lauderdale, FL (US); Ivan Delevic, Key Biscayne, FL (US); Daniel Lieffort, Fort Lauderdale, FL (US); SeongUk Jeon, Guro-gu (KR); Carlos E. Collazo, Old Greenwich, CT (US)

(73) Assignee: Howmedica Osteonics Corp., Mahwah, NJ (US)

( * ) Notice: Subject to any disclaimer, the term of this patent is extended or adjusted under 35 U.S.C. 154(b) by 312 days.

(21) Appl. No.: 18/377,896

(22) Filed: Oct. 9, 2023

(65) Prior Publication Data

US 2024/0032946 A1      Feb. 1, 2024

Related U.S. Application Data

(63) Continuation of application No. 17/069,781, filed on Oct. 13, 2020, now Pat. No. 11,812,978.

(60) Provisional application No. 62/915,017, filed on Oct. 15, 2019.

(51) Int. Cl.
*A61B 17/17* (2006.01)
*A61B 17/16* (2006.01)

(52) U.S. Cl.
CPC ...... *A61B 17/1764* (2013.01); *A61B 17/1624* (2013.01); *A61B 17/1626* (2013.01); *A61B 17/1703* (2013.01)

(58) Field of Classification Search
CPC ............ A61B 17/1764; A61B 17/1624; A61B 17/1626; A61B 17/1703
See application file for complete search history.

(56) References Cited

U.S. PATENT DOCUMENTS

| | | |
|---|---|---|
| 3,727,616 A | 4/1973 | Lenzkes |
| 4,066,082 A | 1/1978 | Arcan et al. |
| 4,092,597 A | 5/1978 | Place |
| 4,127,110 A | 11/1978 | Bullara |
| 4,277,758 A | 7/1981 | Mishiro |
| 4,480,485 A | 11/1984 | Bradshaw et al. |
| 4,731,762 A | 3/1988 | Hanks |
| 4,764,804 A | 8/1988 | Sahara et al. |
| 4,857,893 A | 8/1989 | Carroll |
| 4,899,761 A | 2/1990 | Brown et al. |
| 4,902,958 A | 2/1990 | Cook, II |
| 4,920,279 A | 4/1990 | Charlet et al. |
| 4,983,533 A | 1/1991 | Go |

(Continued)

*Primary Examiner* — Sameh R Boles
(74) *Attorney, Agent, or Firm* — Lerner David LLP

(57) ABSTRACT

A system is disclosed to support installation of a prosthetic joint or a prosthetic component. The system includes at least one sensor to measure a parameter. The system uses one or more patient specific instruments in conjunction with a tensor to make one or more bone cuts. The patient specific instruments and tensor make the bone cuts such that an installed prosthetic joint is aligned, balanced, loaded correctly, and positioned optimally for performance and reliability. The use of the tensor simplifies the workflow required when using the patient specific instruments. In one embodiment, the patient specific instruments are bone cutting jigs configured for the patient anatomy.

18 Claims, 11 Drawing Sheets

(56) References Cited

U.S. PATENT DOCUMENTS

| | | | |
|---|---|---|---|
| 4,986,281 | A | 1/1991 | Preves et al. |
| 5,042,489 | A | 8/1991 | Wiener et al. |
| 5,119,676 | A | 6/1992 | Bower et al. |
| 5,456,724 | A | 10/1995 | Yen et al. |
| 5,470,354 | A | 11/1995 | Hershberger et al. |
| 5,569,260 | A | 10/1996 | Petersen |
| 5,650,571 | A | 7/1997 | Freud et al. |
| 5,669,914 | A | 9/1997 | Eckhoff |
| 5,683,396 | A | 11/1997 | Tokish et al. |
| 5,688,279 | A | 11/1997 | McNulty et al. |
| 5,733,292 | A | 3/1998 | Gustilo et al. |
| 5,871,018 | A | 2/1999 | Delp et al. |
| 5,879,298 | A | 3/1999 | Drobnitzky et al. |
| 5,900,592 | A | 5/1999 | Sohns et al. |
| 6,022,377 | A | 2/2000 | Nuelle et al. |
| 6,072,784 | A | 6/2000 | Agrawal et al. |
| 6,092,530 | A | 7/2000 | Weissman et al. |
| 6,115,636 | A | 9/2000 | Ryan |
| 6,165,142 | A | 12/2000 | Bar |
| 6,184,651 | B1 | 2/2001 | Fernandez et al. |
| 6,245,109 | B1 | 6/2001 | Mendes et al. |
| 6,385,475 | B1 | 5/2002 | Cinquin et al. |
| 6,425,920 | B1 | 7/2002 | Hamada |
| 6,429,585 | B1 | 8/2002 | Kitazume et al. |
| 6,443,891 | B1 | 9/2002 | Grevious |
| 6,447,448 | B1 | 9/2002 | Ishikawa et al. |
| 6,580,947 | B1 | 6/2003 | Thompson |
| 6,583,630 | B2 | 6/2003 | Mendes et al. |
| 6,621,278 | B2 | 9/2003 | Ariav |
| 6,739,068 | B1 | 5/2004 | Rinner |
| 6,758,850 | B2 | 7/2004 | Smith et al. |
| 6,770,078 | B2 | 8/2004 | Bonutti |
| 6,796,988 | B2 | 9/2004 | Melkent et al. |
| 6,856,141 | B2 | 2/2005 | Ariav |
| 6,859,661 | B2 | 2/2005 | Tuke |
| 6,993,393 | B2 | 1/2006 | Von Arx et al. |
| 7,080,554 | B2 | 7/2006 | Ariav et al. |
| 7,097,662 | B2 | 8/2006 | Evans, III et al. |
| 7,141,020 | B2 | 11/2006 | Poland et al. |
| 7,153,281 | B2 | 12/2006 | Holmes |
| 7,173,749 | B2 | 2/2007 | Maleki et al. |
| 7,195,645 | B2 | 3/2007 | Disilvestro et al. |
| 7,195,654 | B2 | 3/2007 | Jackson et al. |
| 7,215,599 | B2 | 5/2007 | Nishimori et al. |
| 7,256,695 | B2 | 8/2007 | Hamel et al. |
| 7,266,989 | B2 | 9/2007 | Ariav |
| 7,283,867 | B2 | 10/2007 | Strother et al. |
| 7,344,493 | B2 | 3/2008 | Sonnenschein et al. |
| 7,347,817 | B2 | 3/2008 | Glukhovsky et al. |
| 7,378,916 | B2 | 5/2008 | Oita et al. |
| 7,384,403 | B2 | 6/2008 | Sherman |
| 7,396,336 | B2 | 7/2008 | Orszulak et al. |
| 7,412,897 | B2 | 8/2008 | Crottet et al. |
| 7,432,788 | B2 | 10/2008 | Glukh et al. |
| 7,442,196 | B2 | 10/2008 | Fisher et al. |
| 7,454,972 | B2 | 11/2008 | Heyman et al. |
| 7,477,926 | B2 | 1/2009 | McCombs |
| 7,481,780 | B2 | 1/2009 | De Guise et al. |
| 7,519,422 | B2 | 4/2009 | Lippert et al. |
| 7,559,951 | B2 | 7/2009 | DiSilvestro et al. |
| 7,575,602 | B2 | 8/2009 | Amirouche et al. |
| 7,578,821 | B2 | 8/2009 | Fisher et al. |
| 7,615,055 | B2 | 11/2009 | DiSilvestro |
| 7,630,774 | B2 | 12/2009 | Karni et al. |
| 7,632,283 | B2 | 12/2009 | Heldreth |
| 7,639,006 | B2 | 12/2009 | Deffeyes |
| 7,643,862 | B2 | 1/2010 | Schoenefeld |
| 7,668,201 | B2 | 2/2010 | Sharony et al. |
| 7,672,726 | B2 | 3/2010 | Ginggen |
| 7,725,288 | B2 | 5/2010 | Boillot |
| 7,769,947 | B2 | 8/2010 | Ranganathan et al. |
| 7,819,826 | B2 | 10/2010 | Diederich et al. |
| 7,918,887 | B2 | 4/2011 | Roche |
| 8,000,926 | B2 | 8/2011 | Roche et al. |
| 8,070,695 | B2 | 12/2011 | Gupta et al. |
| 8,098,544 | B2 | 1/2012 | Roche et al. |
| 8,099,168 | B2 | 1/2012 | Roche |
| 8,141,437 | B2 | 3/2012 | Amirouche et al. |
| 8,167,823 | B2 | 5/2012 | Nycz et al. |
| 8,169,185 | B2 | 5/2012 | Partovi et al. |
| 8,197,489 | B2 | 6/2012 | Chessar et al. |
| 8,197,549 | B2 | 6/2012 | Amirouche et al. |
| 8,211,041 | B2 | 7/2012 | Fisher et al. |
| 8,245,583 | B2 | 8/2012 | Stein |
| 8,270,253 | B1 | 9/2012 | Roche et al. |
| 8,295,920 | B2 | 10/2012 | Bouton et al. |
| 8,372,147 | B2 | 2/2013 | Roche |
| 8,372,153 | B2 | 2/2013 | Roche |
| 8,394,104 | B2 | 3/2013 | DiSilvestro |
| 8,421,479 | B2 | 4/2013 | Stein |
| 8,421,642 | B1 | 4/2013 | McIntosh et al. |
| 8,427,176 | B2 | 4/2013 | Stein |
| 8,444,654 | B2 | 5/2013 | Roche |
| 8,449,556 | B2 | 5/2013 | Roche |
| 8,491,589 | B2 | 7/2013 | Fisher et al. |
| 8,494,805 | B2 | 7/2013 | Roche et al. |
| 8,498,711 | B2 | 7/2013 | Roche |
| 8,516,884 | B2 | 8/2013 | Stein et al. |
| 8,516,907 | B2 | 8/2013 | Stein et al. |
| 8,562,617 | B2 | 10/2013 | Chessar et al. |
| 8,659,661 | B2 | 2/2014 | Frank et al. |
| 8,668,646 | B2 | 3/2014 | Stein et al. |
| 8,679,186 | B2 | 3/2014 | Stein et al. |
| 8,689,647 | B2 | 4/2014 | Stein |
| 8,696,756 | B2 | 4/2014 | Stein et al. |
| 8,701,484 | B2 | 4/2014 | Stein et al. |
| 8,707,782 | B2 | 4/2014 | Stein et al. |
| 8,715,290 | B2 | 5/2014 | Fisher et al. |
| 8,720,270 | B2 | 5/2014 | Stein et al. |
| 8,734,454 | B2 | 5/2014 | DiSilvestro |
| 8,746,062 | B2 | 6/2014 | Stein et al. |
| 8,826,733 | B2 | 9/2014 | Stein et al. |
| 8,926,530 | B2 | 1/2015 | Stein et al. |
| 8,945,133 | B2 | 2/2015 | Stein et al. |
| 8,979,758 | B2 | 3/2015 | Stein et al. |
| 9,119,733 | B2 | 9/2015 | Stein et al. |
| 9,125,627 | B2 | 9/2015 | Stein |
| 9,161,717 | B2 | 10/2015 | Stein et al. |
| 9,226,694 | B2 | 1/2016 | Stein et al. |
| 9,259,172 | B2 | 2/2016 | Stein et al. |
| 9,259,179 | B2 | 2/2016 | Stein |
| 9,265,447 | B2 | 2/2016 | Stein et al. |
| 9,265,462 | B2 | 2/2016 | McIntosh et al. |
| 9,271,675 | B2 | 3/2016 | Stein et al. |
| 9,289,163 | B2 | 3/2016 | Stein et al. |
| 9,301,720 | B2 | 4/2016 | Stein |
| 9,332,943 | B2 | 5/2016 | Stein et al. |
| 9,339,212 | B2 | 5/2016 | Stein et al. |
| 9,345,449 | B2 | 5/2016 | Stein et al. |
| 9,345,492 | B2 | 5/2016 | Stein et al. |
| 9,351,782 | B2 | 5/2016 | Stein et al. |
| 9,357,964 | B2 | 6/2016 | Stein et al. |
| 9,358,136 | B2 | 6/2016 | Stein et al. |
| 9,408,557 | B2 | 8/2016 | Stein et al. |
| 9,456,769 | B2 | 10/2016 | Stein et al. |
| 9,462,964 | B2 | 10/2016 | Stein et al. |
| 9,492,115 | B2 | 11/2016 | Stein et al. |
| 9,492,116 | B2 | 11/2016 | Stein |
| 9,492,119 | B2 | 11/2016 | Stein et al. |
| 9,492,238 | B2 | 11/2016 | Stein et al. |
| 9,566,020 | B2 | 2/2017 | Stein et al. |
| 9,615,887 | B2 | 4/2017 | Stein et al. |
| 9,622,701 | B2 | 4/2017 | Stein et al. |
| 9,642,571 | B2 | 5/2017 | McIntosh et al. |
| 9,642,676 | B2 | 5/2017 | Stein et al. |
| 9,820,678 | B2 | 11/2017 | Stein et al. |
| 9,844,335 | B2 | 12/2017 | Stein et al. |
| 10,004,449 | B2 | 6/2018 | Stein et al. |
| 2002/0029784 | A1 | 3/2002 | Stark et al. |
| 2002/0049394 | A1 | 4/2002 | Roy et al. |
| 2002/0087075 | A1 | 7/2002 | Bucholz |
| 2003/0004518 | A1 | 1/2003 | Perren et al. |
| 2003/0036713 | A1 | 2/2003 | Bouton et al. |
| 2003/0036764 | A1 | 2/2003 | Hamada |

(56) References Cited

U.S. PATENT DOCUMENTS

| | | |
|---|---|---|
| 2003/0069644 A1 | 4/2003 | Kovacevic et al. |
| 2003/0114898 A1 | 6/2003 | Von Arx et al. |
| 2003/0187351 A1 | 10/2003 | Franck et al. |
| 2003/0187452 A1 | 10/2003 | Smith et al. |
| 2004/0011365 A1 | 1/2004 | Govari et al. |
| 2004/0019382 A1 | 1/2004 | Amirouche et al. |
| 2004/0064073 A1 | 4/2004 | Heldreth |
| 2004/0105086 A1 | 6/2004 | Leitner et al. |
| 2004/0131013 A1 | 7/2004 | Ise et al. |
| 2004/0152970 A1 | 8/2004 | Hunter et al. |
| 2004/0184351 A1 | 9/2004 | Nishimori et al. |
| 2004/0215079 A1 | 10/2004 | Omura et al. |
| 2005/0010299 A1 | 1/2005 | Disilvestro |
| 2005/0010302 A1 | 1/2005 | Dietz et al. |
| 2005/0020941 A1 | 1/2005 | Tarabichi |
| 2005/0033383 A1 | 2/2005 | Ibrahim et al. |
| 2005/0234555 A1 | 10/2005 | Sutton et al. |
| 2005/0252294 A1 | 11/2005 | Ariav |
| 2005/0267485 A1 | 12/2005 | Cordes et al. |
| 2005/0273170 A1 | 12/2005 | Navarro et al. |
| 2006/0058798 A1 | 3/2006 | Roman et al. |
| 2006/0069436 A1 | 3/2006 | Sutton et al. |
| 2006/0132120 A1 | 6/2006 | Luber et al. |
| 2006/0161051 A1 | 7/2006 | Terrill-Grisoni et al. |
| 2006/0173295 A1 | 8/2006 | Zeijlemaker |
| 2006/0184067 A1 | 8/2006 | Clark et al. |
| 2006/0195042 A1 | 8/2006 | Flaherty |
| 2006/0206014 A1 | 9/2006 | Ariav |
| 2006/0232408 A1 | 10/2006 | Nycz et al. |
| 2006/0241422 A1 | 10/2006 | Muratayev et al. |
| 2006/0241569 A1 | 10/2006 | DiSilvestro |
| 2006/0265026 A1 | 11/2006 | Madjar et al. |
| 2006/0271112 A1 | 11/2006 | Martinson et al. |
| 2007/0005145 A1 | 1/2007 | Banks et al. |
| 2007/0089518 A1 | 4/2007 | Ericson et al. |
| 2007/0129776 A1 | 6/2007 | Robins et al. |
| 2007/0173946 A1 | 7/2007 | Bonutti |
| 2007/0219561 A1 | 9/2007 | Lavallee et al. |
| 2007/0233065 A1 | 10/2007 | Donofrio et al. |
| 2007/0233267 A1 | 10/2007 | Amirouche et al. |
| 2007/0234819 A1 | 10/2007 | Amirouche et al. |
| 2007/0239165 A1 | 10/2007 | Amirouche |
| 2007/0239282 A1 | 10/2007 | Caylor et al. |
| 2007/0242652 A1 | 10/2007 | Dahlman et al. |
| 2007/0255088 A1 | 11/2007 | Jacobson et al. |
| 2007/0258674 A1 | 11/2007 | Wang et al. |
| 2007/0272747 A1 | 11/2007 | Woods et al. |
| 2007/0276294 A1 | 11/2007 | Gupta et al. |
| 2007/0282451 A1 | 12/2007 | Metzger et al. |
| 2008/0051908 A1 | 2/2008 | Angibaud et al. |
| 2008/0082118 A1 | 4/2008 | Edidin et al. |
| 2008/0129486 A1 | 6/2008 | Jeckelmann et al. |
| 2008/0133016 A1 | 6/2008 | Heinz |
| 2008/0191584 A1 | 8/2008 | Malkin et al. |
| 2008/0228195 A1 | 9/2008 | von Jako et al. |
| 2008/0228231 A1 | 9/2008 | Raphael et al. |
| 2008/0243266 A1 | 10/2008 | Haynes et al. |
| 2009/0005708 A1 | 1/2009 | Johanson et al. |
| 2009/0069803 A1 | 3/2009 | Starkebaum |
| 2009/0167719 A1 | 7/2009 | Woolley |
| 2009/0264894 A1 | 10/2009 | Wasielewski |
| 2009/0299483 A1 | 12/2009 | Amirouche et al. |
| 2010/0010494 A1 | 1/2010 | Quirno |
| 2010/0022874 A1 | 1/2010 | Wang et al. |
| 2010/0076505 A1 | 3/2010 | Borja |
| 2010/0076563 A1 | 3/2010 | Otto et al. |
| 2010/0100010 A1 | 4/2010 | Andarawis et al. |
| 2010/0100130 A1 | 4/2010 | Carl et al. |
| 2010/0151946 A1 | 6/2010 | Wilson et al. |
| 2010/0191153 A1 | 7/2010 | Sanders et al. |
| 2010/0198067 A1 | 8/2010 | Mahfouz et al. |
| 2010/0204575 A1 | 8/2010 | Roche et al. |
| 2010/0204955 A1 | 8/2010 | Roche et al. |
| 2010/0249665 A1 | 9/2010 | Roche |
| 2010/0249787 A1 | 9/2010 | Roche |
| 2010/0249788 A1 | 9/2010 | Roche |
| 2010/0249790 A1 | 9/2010 | Roche |
| 2010/0249791 A1 | 9/2010 | Roche |
| 2010/0250571 A1* | 9/2010 | Pierce .................. A61B 5/4528 600/587 |
| 2010/0320973 A1 | 12/2010 | Nishida |
| 2010/0328098 A1 | 12/2010 | Stein et al. |
| 2010/0331633 A1 | 12/2010 | Stein |
| 2010/0331680 A1 | 12/2010 | Stein |
| 2010/0331682 A1 | 12/2010 | Stein et al. |
| 2010/0331734 A1 | 12/2010 | Stein |
| 2010/0331735 A1 | 12/2010 | Stein |
| 2010/0331736 A1 | 12/2010 | Stein |
| 2010/0331737 A1 | 12/2010 | Stein et al. |
| 2010/0331738 A1 | 12/2010 | Stein et al. |
| 2011/0004076 A1 | 1/2011 | Janna et al. |
| 2011/0029913 A1 | 2/2011 | Boillot et al. |
| 2011/0032184 A1 | 2/2011 | Roche et al. |
| 2011/0060220 A1 | 3/2011 | Roche et al. |
| 2011/0092972 A1 | 4/2011 | Allen |
| 2011/0102455 A1 | 5/2011 | Temple |
| 2011/0107850 A1 | 5/2011 | Kim et al. |
| 2011/0160572 A1 | 6/2011 | McIntosh et al. |
| 2011/0160616 A1 | 6/2011 | Stein et al. |
| 2011/0160738 A1 | 6/2011 | McIntosh et al. |
| 2011/0257491 A1 | 10/2011 | Robertson et al. |
| 2011/0275957 A1 | 11/2011 | Bhandari |
| 2012/0016362 A1 | 1/2012 | Heinrich et al. |
| 2012/0022667 A1 | 1/2012 | Accinni et al. |
| 2012/0035868 A1 | 2/2012 | Roche et al. |
| 2012/0147887 A1 | 6/2012 | Fan et al. |
| 2012/0209117 A1 | 8/2012 | Mozes et al. |
| 2012/0330367 A1 | 12/2012 | Roche et al. |
| 2013/0023794 A1 | 1/2013 | Stein et al. |
| 2013/0023795 A1 | 1/2013 | Stein et al. |
| 2013/0079668 A1 | 3/2013 | Stein et al. |
| 2013/0079670 A1 | 3/2013 | Stein et al. |
| 2013/0079671 A1 | 3/2013 | Stein et al. |
| 2013/0079675 A1 | 3/2013 | Stein et al. |
| 2013/0079884 A1 | 3/2013 | Stein et al. |
| 2013/0225982 A1 | 8/2013 | McIntosh et al. |
| 2013/0226036 A1 | 8/2013 | Stein et al. |
| 2014/0094715 A1 | 4/2014 | Stein et al. |
| 2014/0134586 A1 | 5/2014 | Stein et al. |
| 2014/0135624 A1 | 5/2014 | Stein et al. |
| 2014/0135655 A1 | 5/2014 | Stein et al. |
| 2014/0135773 A1 | 5/2014 | Stein et al. |
| 2014/0276886 A1 | 9/2014 | Stein et al. |
| 2014/0288563 A1 | 9/2014 | Claypool et al. |
| 2016/0157940 A1 | 6/2016 | Stein et al. |

* cited by examiner

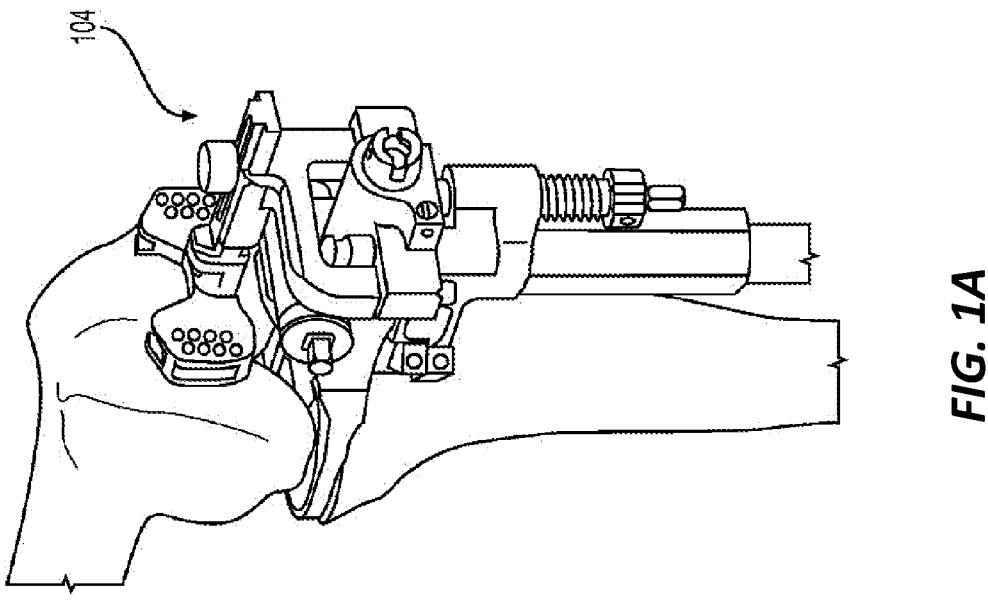
*FIG. 1A*
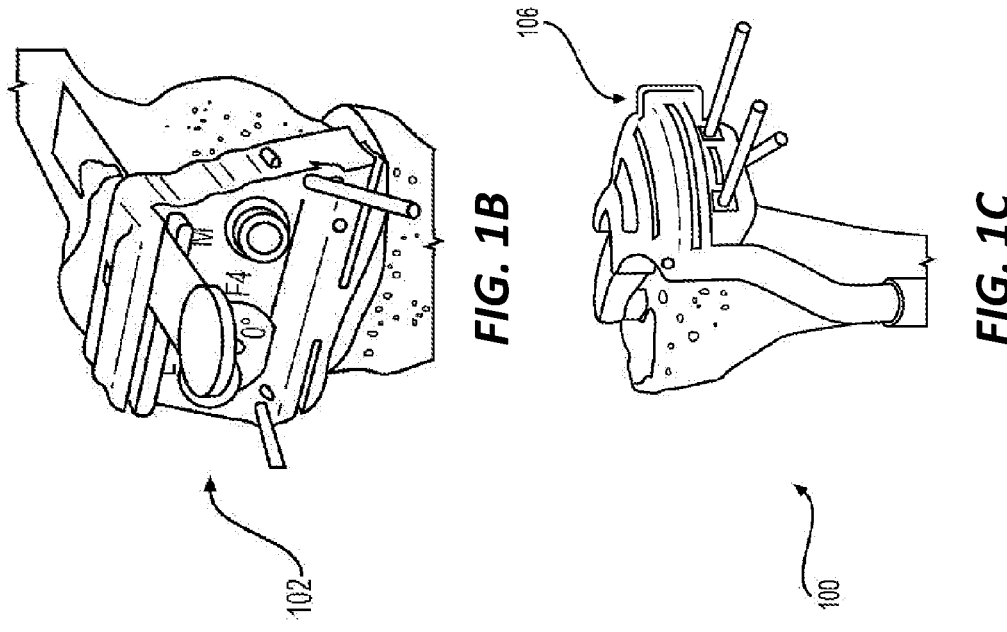
*FIG. 1B*
*FIG. 1C*

KNEE BALANCING SYSTEM USING PATIENT SPECIFIC INSTRUMENTATION

CROSS-REFERENCE TO RELATED APPLICATIONS

This application is a continuation of U.S. application Ser. No. 17/069,781, filed on Oct. 13, 2020, which claims the benefit of the filing date of U.S. Provisional Patent Application No. 62/915,017 filed on Oct. 15, 2019, the disclosures of which are hereby incorporated herein by reference.

FIELD

The present invention pertains generally to measurement of physical parameters, and particularly to, but not exclusively, medical electronic devices for high precision sensing.

BACKGROUND

The skeletal system of a mammal is subject to variations among species. Further changes can occur due to environmental factors, degradation through use, and aging. An orthopedic joint of the skeletal system typically comprises two or more bones that move in relation to one another. Movement is enabled by muscle tissue and tendons attached to the skeletal system of the joint. Ligaments hold and stabilize the one or more joint bones positionally. Cartilage is a wear surface that prevents bone-to-bone contact, distributes load, and lowers friction.

There has been substantial growth in the repair of the human skeletal system. In general, orthopedic joints have evolved using information from simulations, mechanical prototypes, and patient data that is collected and used to initiate improved designs. Similarly, the tools being used for orthopedic surgery have been refined over the years but have not changed substantially. Thus, the basic procedure for replacement of an orthopedic joint has been standardized to meet the general needs of a wide distribution of the population. Although the tools, procedure, and artificial joint meet a general need, each replacement procedure is subject to significant variation from patient to patient. The correction of these individual variations relies on the skill of the surgeon to adapt and fit the replacement joint using the available tools to the specific circumstance.

BRIEF DESCRIPTION OF THE DRAWINGS

Various features of the system are set forth with particularity in the appended claims. The embodiments herein, can be understood by reference to the following description, taken in conjunction with the accompanying drawings, in which:

FIGS. 1A-1C is an illustration of a system of patient specific instruments in accordance with an example embodiment;

DETAILED DESCRIPTION

Figures 2A, 2B:
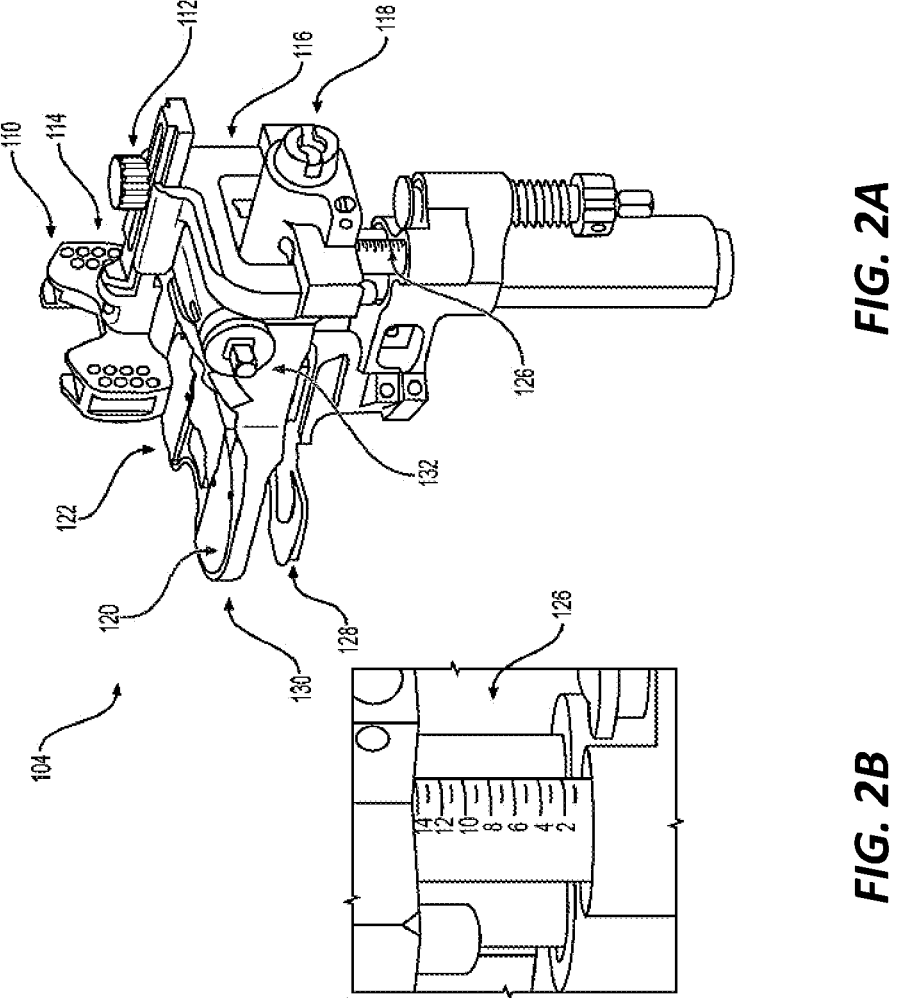
FIG. 2A is an illustration of the tensor in accordance with an example embodiment.
FIG. 2B is a close-up view of a distraction gap display of the tensor of FIG. 2A.

Embodiments of the invention are broadly directed to measurement of physical parameters, and more particularly, to fast-response circuitry that supports accurate measurement of small sensor changes in a surgical environment.

The following description of exemplary embodiment(s) is merely illustrative in nature and is in no way intended to limit the invention, its application, or uses.

For simplicity and clarity of the illustration(s), elements in the figures are not necessarily to scale, are only schematic and are non-limiting, and the same reference numbers in different figures denote the same elements, unless stated otherwise. Additionally, descriptions and details of well-known steps and elements are omitted for simplicity of the description. Notice that once an item is defined in one figure, it may not be discussed or further defined in the following figures.

The terms "first", "second", "third" and the like in the Claims or/and in the Detailed Description are used for distinguishing between similar elements and not necessarily for describing a sequence, either temporally, spatially, in ranking or in any other manner. It is to be understood that the terms so used are interchangeable under appropriate circumstances and that the embodiments described herein are capable of operation in other sequences than described or illustrated herein.

Processes, techniques, apparatus, and materials as known by one of ordinary skill in the art may not be discussed in detail but are intended to be part of the enabling description where appropriate.

The orientation of the x, y, and z-axes of rectangular Cartesian coordinates is assumed to be such that the x and y axes define a plane at a given location, and the z-axis is normal to the x-y plane. The axes of rotations about the Cartesian axes of the device are defined as yaw, pitch and roll. With the orientation of the Cartesian coordinates defined in this paragraph, the yaw axis of rotation is the z-axis through body of the device. Pitch changes the orientation of a longitudinal axis of the device. Roll is rotation about the longitudinal axis of the device. The orientation in Cartesian coordinates is selected to facilitate graphical display on computer screens or displays having the orientation that the user will be able to relate to most easily. Therefore the image of the device moves upward on the computer display whenever the device itself moves upward for example away from the surface of the earth. The same applies to movements to the left or right.

Although inertial sensors are provided as enabling examples in the description of embodiments, any tracking device (e.g., a GPS chip, acoustical ranging, accelerometer, magnetometer, gyroscope, inclinometers, MEMs devices) can be used within the scope of the embodiments described.

At least one embodiment is directed to a kinetic orthopedic measurement system to aid a surgeon in determining real time alignment, range of motion, loading, impingement, and contact point of orthopedic implants. Although the system is generic to any orthopedic surgery (e.g., spinal, shoulder, knee, hip, ankle, wrist, finger, toe, bone, musculoskeletal, etc.) the following examples deal with knee surgery as a non-limiting example of an embodiment of the invention.

The non-limiting embodiment described herein is related to quantitative measurement based orthopedic surgery and referred to herein as the kinetic system. The kinetic system includes a sensor system that provides quantitative measurement data and feedback that can be provided visually, audibly, or haptically to a surgeon or surgical team. The kinetic system provides the surgeon real-time dynamic data regarding force, pressure, or loading on the knee joint, contact and congruency through a full range of motion.

In general, kinetics is the study of the effect of forces upon the motion of a body or system of bodies. Disclosed herein is a system for kinetic assessment of the musculoskeletal system. The kinetic system can be for the installation of prosthetic components or for monitoring and assessment of permanently installed components to the musculoskeletal system. For example, installation of a prosthetic component can require one or more bone surface to be prepared to receive a device or component. The kinetic system is designed to take quantitative measurements of at least the load, position of load, or alignment with the forces being applied to the joint similar to that of a final joint installation. The sensored measurement components are designed to allow ligaments, tissue, and bone to be in place while the quantitative measurement data is taken. This is significant because the bone cuts take into account the kinetic forces where a kinematic assessment and subsequent bone cuts could be substantial changed from an alignment, load, and position of load once the joint is reassembled.

A prosthetic joint installation can benefit from quantitative measurement data in conjunction with subjective feedback of the prosthetic joint to the surgeon. The quantitative measurements can be used to determine adjustments to bone, prosthetic components, or tissue prior to final installation. Permanent sensors can also be housed in final prosthetic components to provide periodic data related to the status of the implant. Data collected intra-operatively and long term can be used to determine parameter ranges for surgical installation and to improve future prosthetic components. The physical parameter or parameters of interest can include, but are not limited to, measurement of alignment, load, force, pressure, position, displacement, density, viscosity, pH, spurious accelerations, color, movement, particulate matter, structural integrity, and localized temperature. Often, several measured parameters are used to make a quantitative assessment. A graphical user interface can support assimilation of measurement data. Parameters can be evaluated relative to orientation, alignment, direction, displacement, or position as well as movement, rotation, or acceleration along an axis or combination of axes by wireless sensing modules or devices positioned on or within a body, instrument, appliance, vehicle, equipment, or other physical system.

While the specification concludes with claims defining the features of the invention that are regarded as novel, it is believed that the invention will be better understood from a consideration of the following description in conjunction with the drawing figures, in which like reference numerals are carried forward.

The example embodiments shown herein below of the measurement device are illustrative only and do not limit use for other parts of a body. The measurement device can be a tool, equipment, implant, or prosthesis that measures at least one parameter or supports installation of prosthetic components to the musculoskeletal system. The measurement device can be used on bone, the knee, hip, ankle, spine, shoulder, hand, wrist, foot, fingers, toes, and other areas of the musculoskeletal system. In general, the principles disclosed herein are meant to be adapted for use in all locations of the musculoskeletal system.

At least one embodiment is directed to a system for distracting and balancing a knee joint in at least two positions to support bone cuts for installation of one or more prosthetic components. The system further includes patient specific instruments that are customized for the specific patient. In one embodiment, the patient specific instruments comprise one or more bone cutting guides to support one or more bone cuts. The system has at least one articular surface that supports movement when inserted in the joint. The system further includes a plurality of load sensors coupled to the articular surface and a position measurement system configured to measure position, slope, rotation, or trajectory. The system has computer and display configured to wirelessly receive quantitative measurement data from the system inserted in the joint where the computer and display is configured to display the articular surface, to display position of applied load to the articular surface, contact point rotation relative to a reference position, load magnitude at the position of applied load (contact point), range of motion, and other sensor information. The system provides the information on the display in the operating room in real-time to support the installation process to optimize the surgery for performance, reduced rehabilitation, stability, and reliability.

In all of the examples illustrated and discussed herein, any specific materials, such as temperatures, times, energies, and material properties for process steps or specific structure implementations should be interpreted to be illustrative only and non-limiting. Processes, techniques, apparatus, and materials as known by one of ordinary skill in the art may not be discussed in detail but are intended to be part of an enabling description where appropriate. It should also be noted that the word "coupled" used herein implies that elements may be directly coupled together or may be coupled through one or more intervening elements.

Additionally, the sizes of structures used in exemplary embodiments are not limited by any discussion herein (e.g., the sizes of structures can be macro (centimeter, meter, and larger sizes), micro (micrometer), and nanometer size and smaller).

Notice that similar reference numerals and letters refer to similar items in the following figures, and thus once an item is defined in one figure, it may not be discussed or further defined in the following figures.

FIGS. 1A-1C illustrate a system 100 of patient specific instruments in accordance with an example embodiment. Patient specific instruments are used in conjunction with a tensor 104 (FIG. 1A) configured for patient specific balance prior to one or more bone cuts. In general, patient specific instruments (PSI) are configured to simplify and support the installation of one or more prosthetic components during implant surgery. In one embodiment, a patient specific instrument is a custom instrument designed specifically for a patient bone geometry and deformities to optimize a prosthetic component installation for performance and reliability whereas most prosthetic component installations are not optimized for a patient but to accommodate a wide range of people at the detriment of performance or reliability. In one embodiment, a PSI is a cutting block customized for a bone structure of a patient. The PSI cutting block is designed using images such as computed tomography (CT), X-rays, magnetic resonance imaging (MRI), ultrasonic imaging, other imaging techniques, or combinations of different images to render a 3D model of the musculoskeletal system. As mentioned previously, the PSI cutting block can take into account bone deformities as well as osteophytes. The 3D model can also be used in a preplan to facility or determine an implementation of a bone resection. Having modeled the musculoskeletal system during the preplanning stage, the PSI cutting block can be customized for different traumas that may have occurred to a bone or bones of the musculoskeletal system such as fractures or mal-alignment. The preplanning can take into account the trauma or mal-alignment using the 3D model such that a workflow can be generated to bring the musculoskeletal system back into alignment as well as determining if problems can occur using standard prosthetic components. The 3D model can support a selection of implant size, position, and rotation thereby reducing surgical time in the operating room which is more efficient and saves costs. In one embodiment, the PSI can be manufactured using 3D printers to build the custom instrument using measurements from the 3D models of the musculoskeletal system.

System 100 comprises a bone cutting jig 102 configured to couple to a patient femur (FIG. 1B), a bone cutting jig 106 configured to couple to the patient tibia (FIG. 1C), and a tensor 104 configured to distract, load, balance, and support a bone cut. In the example, system 100 supports one or more bone cuts to install a knee prosthetic joint that is loaded correctly, balanced, and aligned. Although a knee prosthetic component is used in the example, system 100 can be adapted for use in hip, ankle, shoulder, spine, hand, wrist, and other parts of the musculoskeletal system requiring one or more bone cuts for installing a prosthetic component. In one embodiment, bone cutting jig 106 is a patient specific instrument configured to couple to the patient.

System 100 combines the advantages of pre-operative planning, generating a 3D model of a patient specific musculoskeletal system, and alignment capabilities of patient specific instruments with predictive implant balancing of tensor 104. Tensor 104 is configured to enable patient specific instrument guide placement for optimal femoral implant location. The workflow disclosed herein simplifies and differentiates from other instrument systems or procedures using existing technology. Moreover, predictive balancing of the knee joint at the native femoral step enables intraoperative efficiency by preventing the need for any re-cuts or adjustments.

FIG. 2A is an illustration of tensor 104 in accordance with an example embodiment. Tensor 104 is modified to work with one or more patient specific instruments to support installation of one or more prosthetic components. In one embodiment, tensor 104 is configured to enable implant planning non-robotically by adding femoral drill guide 110 that corresponds to the patient specific instruments. Femoral drill guide 110 relates to bone cutting jig 102 and bone cutting jig 106 shown in FIGS. 1A-1C. Drill guide 110 is configured to be utilized to set balanced extension and flexion femoral implant location. A modular drill guide attachment 116 is configured to couple to tensor 104. Modular drill guide attachment 116 includes an anterior/posterior (A/P) adjustment 112 for femoral drill guide 110 and a rotation adjustment 114 for femoral drill guide 110.

Tensor 104 comprises a tibial plate 128, a femoral plate 130, a distraction mechanism 118, a tilt mechanism 132, electronic circuitry, and one or more sensors. Tibial plate 128 is configured to couple to a tibia and femoral plate 130 is configured to couple to a femur. More specifically, femoral plate 130 has a medial side and a lateral side configured to respectively couple to a medial femoral condyle and a lateral femoral condyle of the femur. In one embodiment, a load plate 120 and a load plate 122 couples to femoral plate 130. In one embodiment, the electronic circuitry and the one or more sensors underlie at least in part, load plates 120 and 122. The one or more sensors couple to the electronic circuitry. The electronic circuitry controls a measurement process and transmits measurement data to a computer in the operating room The computer includes a display configured to display measurement from tensor 104 in real-time.

Femoral plate moves 130 in relation to tibial plate 128 to distract a tibia from a femur by a predetermined distance. A surgeon couples a device having a handle to distraction mechanism 118. The device is used to rotate distraction mechanism to raise or lower femoral plate 130 relative to tibial plate 128. A distraction gap display 126 is provided on tensor 104 to quantify the distraction gap. An enlarged region of the distraction gap display 126 is also illustrated in FIG. 2B showing hash marks indicated the amount of distraction. As mentioned previously, femoral plate 130 includes load sensors for measuring load applied to tensor 104. Loading applied to load plate 120 is measured independently from the loading applied to load plate 122. In one embodiment, three or more sensors underlie load plate 120 to support a load measurement. Similarly, three or more load sensors underlie load plate 122. The load sensors can be used to determine a load magnitude at each sensor location. A load magnitude applied at a contact point on either load plate 120 or load plate 122 can be calculated using the position of each sensor underlying the load plate and the load magnitude at the location. Thus, the point of contact to the load plate and the load magnitude at the point of contact can be determined and displayed by the computer in real-time. Overall cut to cut gap is displayed allowing extension and flexion gap balancing.

Figures 3A, 3B, 3C, 3D:
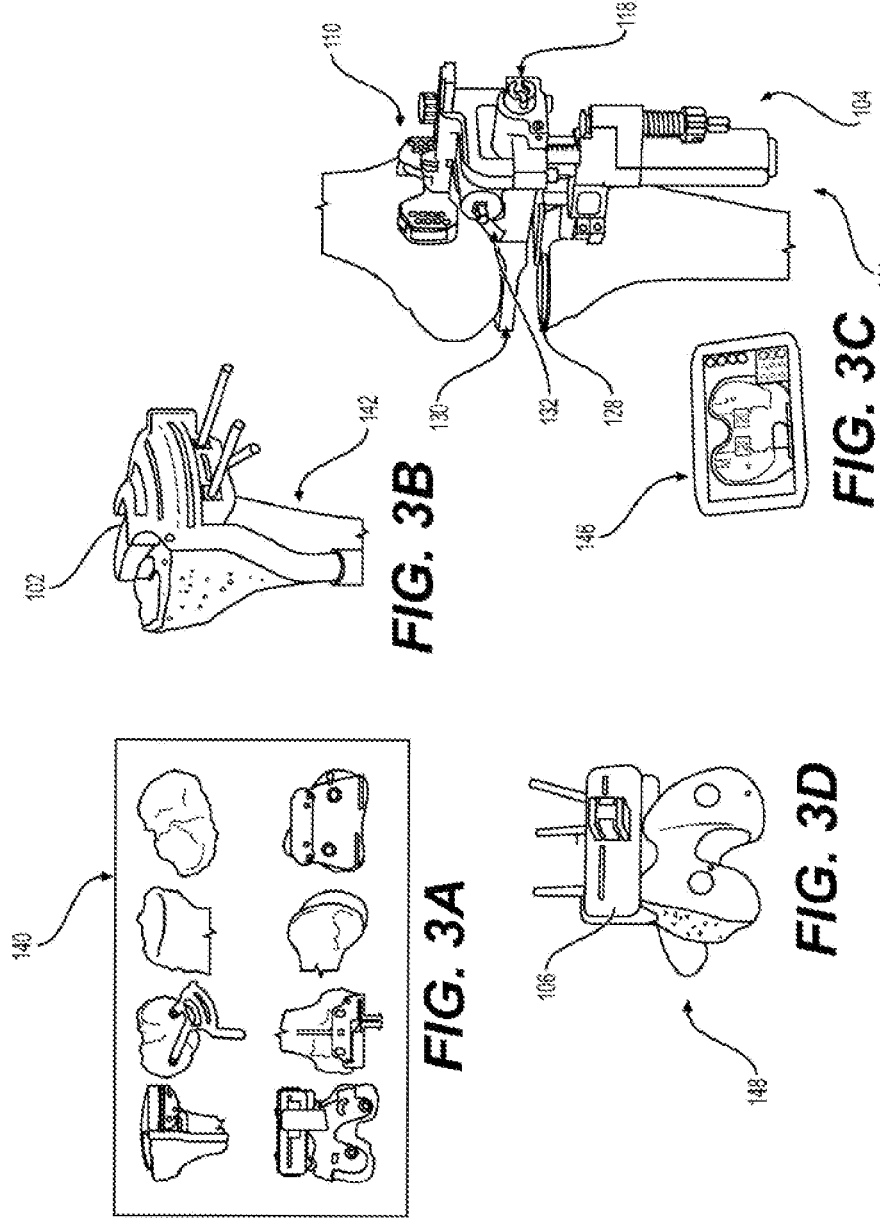
FIGS. 3A-3G is an illustration of a clinical workflow using patient specific instruments with the tensor in accordance with an example embodiment.

FIGS. 3A-3G illustrate of a clinical workflow using patient specific instruments with tensor 104 in accordance with an example embodiment. The workflow comprises one or more steps using one or more patient specific instruments and tensor 104 to support installation of one or more prosthetic components. The steps can be performed in any order and no sequence is implied. Steps can be removed or replaced in the workflow depending on the application. FIG. 3A is an illustration of a pre-operative plan in accordance with an example embodiment. In a step 140, a display shows a preoperative plan for the installation of one or more prosthetic components to a surgical team in an operating room. In general, a surgeon or surgical team goes through a standard pre-operative planning process prior to the surgery. In the example, the planning includes optimization of tibial or femoral location. The PSI will be manufactured for the patient during the pre-operative planning phase. In one embodiment, this will comprise one or more cutting blocks that are configured to couple to the patient based on a 3D model of the musculoskeletal system. The bone cuts and joint reconstruction can be optimized for the specific patient using the 3D model and identified deformities, trauma, injury, bone growths, or other factors that could impact the surgery. In one embodiment, the pre-operative plan can be displayed on the display of computer 146 shown in FIG. 3C in the operating room to provide unique information related to the patient or changes to the workflow due to specifics of the patient.

FIG. 3B is an illustration of a bone cutting jig 102 in accordance with an example embodiment. Bone cutting jig 102 is a PSI built for the patient undergoing surgery using image data and a 3D model of the musculoskeletal system. In a step 142, bone cutting jig 102 is used to resect a proximal tibia. Bone cutting jig 102 is a patient specific instrument and a tibial resection guide. In one embodiment, the bone cut to the tibia is performed to be in alignment with the mechanical axis of the leg. Alternatively, the bone cut can take into account deformities in the leg to improve stability, performance, and reliability of the joint installation.

FIG. 3C is an illustration of a tensor 104 inserted in a knee joint of the musculoskeletal system in accordance with an example embodiment. In one embodiment, tensor 104 is placed in at a minimum height. Tensor 104 is placed in the knee joint such that tibial plate 128 couples to the prepared surface of the tibia and a medial side and a lateral side of femoral plate 130 respectively couples to a medial condyle and a lateral condyle of the femur. In a step 144, medial and lateral forces are balanced in the knee joint. A balancing process uses distraction mechanism 118 and tilt mechanism 132 of tensor 104. Distraction mechanism 118 is rotated to increase or decrease the medial and lateral compartment heights. Tilt mechanism 132 is rotated to tilt femoral plate 130 to further adjust the loading on the medial side and the lateral side of femoral plate 130. Tilt mechanism 132 will also change the medial and lateral compartment heights but can change them such that the compartment heights differ. In general, the leg is placed in flexion in a position greater than 5 degrees but less than 80 degrees. In one embodiment, the leg is positioned in approximately 10 degrees flexion with tensor 104 inserted in the knee joint. In one embodiment, the forces on the medial and lateral sides of the knee are balanced. Sensors on the medial and lateral side of femoral plate 130 measure a load magnitude at the point of contact respectively of the medial condyle and the lateral condyle of the femur. In one embodiment, the load measurements and contact point information is displayed on computer 146 in real-time for a surgical team to view. In one embodiment, balance does not mean making the loading applied by the musculoskeletal system to tensor 104 equal on the medial and lateral sides. In one embodiment, balance can be setting the loading on the medial side of tensor 104 to a first predetermined load magnitude and setting the loading on the lateral side of tensor 104 to a second predetermined load magnitude based on the pre-operative plan, the type of implant used, or what is determined during surgery. Once the balance has been established, the knee joint or the leg is moved and checked at full extension. Additional steps can be performed to optimize the knee if the knee joint hyperextends when placed in full extension or if the knee does not extend to full extension. For example, tissue tensioning, bone cuts, or compartment adjustments can be performed to increase or decrease knee joint movement to prevent hyperextension but allowing the leg to reach full extension. In one embodiment, one or more sensors within tensor 104 transmit measurement data to a computer 146. In one embodiment, computer 146 receives, calculates, and processes the measurement data to provide an output in a visual, audible, or haptic form that supports rapid data assimilation of the information. Computer 146 has a display in the operating room to provide the measurement data in real-time to the surgeon and surgical team. Computer 146 and the display can indicate issues or problems from the measurement data. Furthermore, computer 146 can suggest one or more workflow steps to address an issue or improve the installation. The distraction gap indicator is referenced and one or more holes are drilled using femoral drill guide 110 when the knee joint is balanced and tested that the leg can move to full extension. In one embodiment, femoral drill guide 110 supports cutting the femur to allow equal compartment heights with the leg in full extension and in balance. The tensor 104 is returned to the minimum height and removed from the knee joint.

FIG. 3D is an illustration of PSI cutting block 106 coupled to the femur in accordance with an example embodiment. In a step 148, bone cutting jig 106 is pinned to the femur using the one or more holes drilled using femoral drill guide 110 on tensor 104 as shown in FIG. 3C. Bone cutting jig 106 is a patient specific instrument that was manufactured using the 3D imaging of the musculoskeletal as described herein above. The femur is than resected using bone cutting jig 106.

Figures 3E, 3F, 3G:
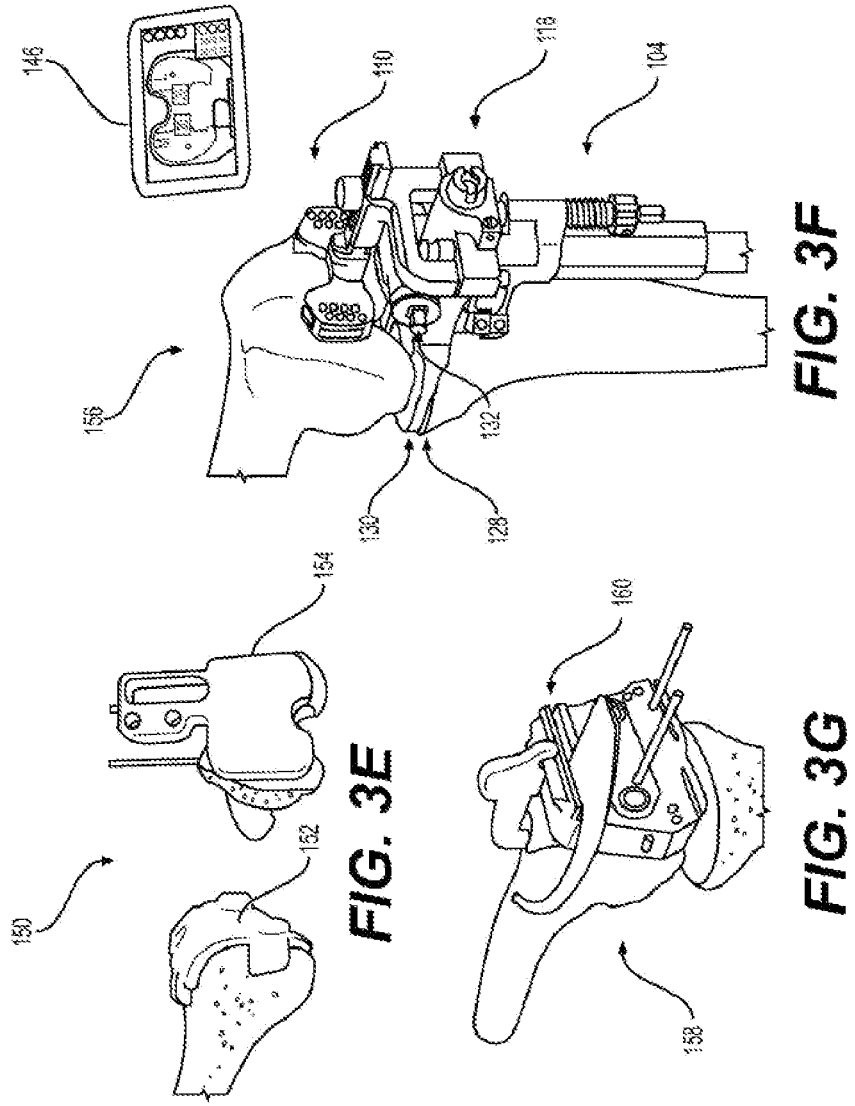

FIG. 3E is an illustration of a coronal alignment check in accordance with an example embodiment. In a step 150, a coronal alignment check can be made before or after resection. In one embodiment, a femoral PSI 152 is coupled to the femur to support coronal alignment measurement. In one embodiment, a tibial PSI 154 is coupled to the tibia to support the coronal alignment measurement.

FIG. 3F is an illustration of tensor 104 placed in the knee joint with the leg in flexion in accordance with an example embodiment. In a step 156, the leg is balanced in flexion. In general, the leg is placed in flexion at greater than 80 degrees but less than 145 degrees. In one embodiment, the leg is flexed to approximately 90 degrees. Tensor 104 is placed at minimum height and inserted into the knee joint in flexion. Distractor mechanism 118 is used to set the compartment height. Tilt mechanism 132 is used to tilt femoral plate 130 to achieve balance with the leg in flexion. In one embodiment, the balance forces are based on patient specific forces or determined when the leg was placed in extension in the prior balancing step (with the leg in extension). Measurement data is displayed on computer 146 in real-time. The distraction gap indicator is referenced and one or more holes are drilled using femoral drill guide 110 to support pinning a desired thickness in flexion matching the extension target (i.e. 18, 19, 20 mm etc. . . . ). In one embodiment, the medial and lateral compartment heights of the knee joint at 90 degrees flexion can be made identical to the medial and lateral compartment height at full extension. Alternatively, they can be made having compartment heights that differ. The complexity can change significantly using PSI prosthetic components. Tensor 104 is removed from the knee joint after the balancing distraction gap is reduced.

FIG. 3G is an illustration of bone cutting jig 160 coupled to the femur in accordance with an example embodiment. In a step 158, a bone cutting jig 160 is pinned to the femur in flexion. Bone cutting jig 160 is a patient specific instrument and is configured to remove posterior bone from a distal end of the femur. The resection depths are confirmed prior to a cut being made. Bone cutting jig 160 is pinned to the femur using the one or more holes drilled using femoral drill guide 110 when the leg was placed at 90 degrees flexion. The femoral cuts are then performed to the femur in flexion thereby removing a portion of the posterior side of the distal end of the femur. The tibial prosthetic component, femoral prosthetic component, and the insert can then be installed to complete the prosthetic knee surgery with the knee in balance based on quantitative measurement data from tensor 104.

Patient specific instrument enable all implant and instrument sizing to be pre-determined, minimal reusables, patient kitted (one sensor) disposable system. Predictively balancing the joint at the native femoral step enables intraoperative efficiency by preventing the need for any re-cuts or adjustments. A patient specific instrumentation surgical plan could be displayed within a tablet or computer for reference throughout the surgery. The workflow is a significant advance compared to other patient specific instrument products. The system enables intraoperative flexibility that is not possible with patient specific instrument products alone. In one embodiment, the tensor can be adapted for use with a surgical robot.

Figures 4A, 4B:
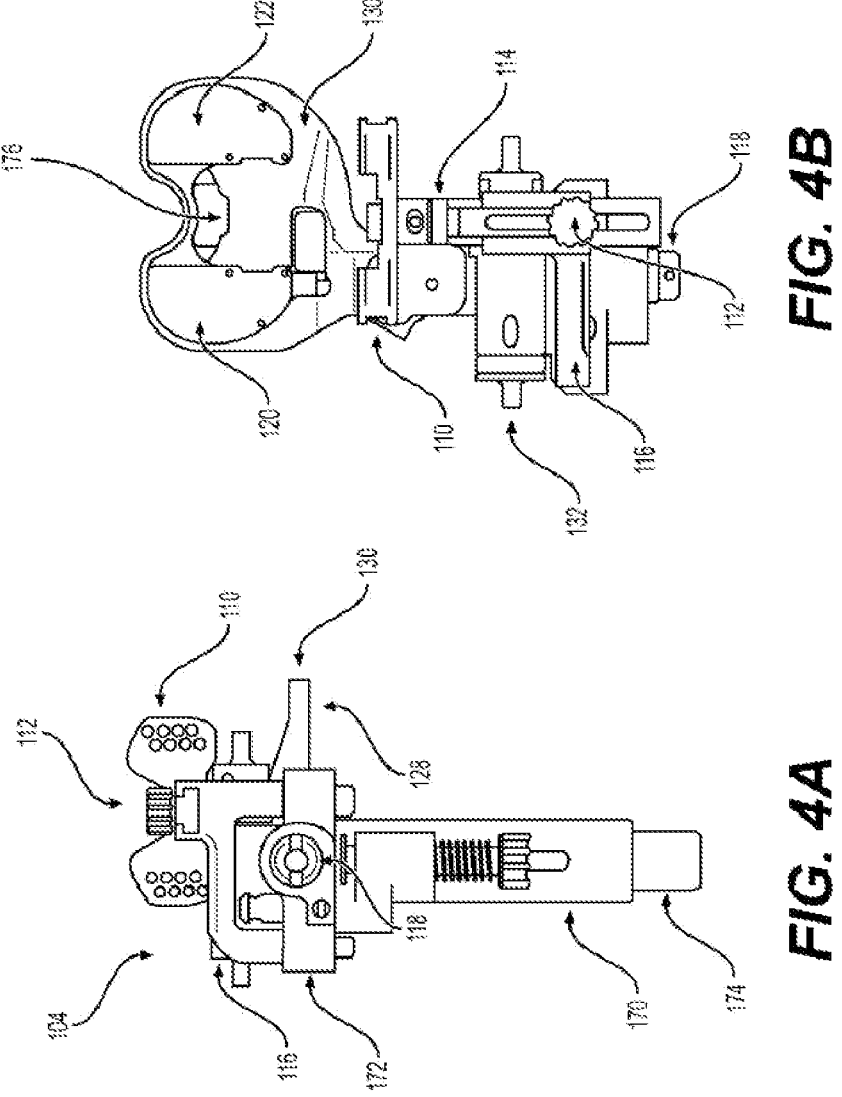
FIGS. 4A-4D are illustrations of different views of the tensor in accordance with an example embodiment.

FIG. 4A-4D illustrates different views of tensor 104 in accordance with an example embodiment. FIG. 4A is an illustration of an anterior view of tensor 104 in accordance with an example embodiment. In one embodiment, tibial plate 128 is configured to couple to femoral plate 130 when tensor 104 is in a minimum height position. In one embodiment, tibial plate 128 is smaller or comprises less area than femoral plate 130. In one embodiment, a bottom surface of femoral plate 130 includes a cavity. Tibial plate 128 fits within the cavity of the bottom surface of femoral plate 130 to minimize the minimum height. Femoral plate 130 and tibial plate 128 are inserted within the knee joint. Femoral plate 130 is a moving structure whereas tibial plate 128 is in a fixed position. Tibial plate 128 couples to tube 170. Tube 170 is directed in a reference position of tensor 104. In one embodiment, tibial plate 128 is affixed to tube 170 at a 90 degree angle relative to the direction of tube 170. In one embodiment, a bottom surface of tibial plate 128 is planar to couple to a prepared bone surface of a tibia. An upper surface of tibial plate 128 can include ribbing or other structures to increase a rigidity of tibial plate 128.

A tool is configured to couple to distraction mechanism 118. The tool is inserted and aligned to distraction mechanism 118 to support rotating distraction mechanism 118 by a surgeon. In one embodiment, femoral plate 130 couples to cylindrical structure 174 and at least a portion of cylindrical structure 174 is inserted into tube 170. In one embodiment, distraction mechanism 118 is a gear mechanism configured to raise and lower the cylindrical structure thereby raising and lowering femoral plate 130. A side of the cylindrical structure 174 can have gear teeth configured to couple to the gear mechanism of distraction mechanism 118 to support raising or lowering femoral plate 130. The surgeon viewing the anterior view of tensor 104 can see the distraction gap display 126 (shown in FIG. 2A). Alternatively, tensor 104 can have a sensor system configured to measure and display the distraction gap or the compartment gaps on the medial and lateral sides of tensor 104. In one embodiment, the distraction gap would be displayed on the display of computer 146 (as shown in FIG. 3C) in the operating room. Thus, the surgeon and surgical team can view the contact points, load magnitudes, distraction gap, and tilt of femoral plate 30 in real-time during the surgery.

In one embodiment, femoral plate 130 couples to support structure 172. Support structure 172 couples to cylindrical structure 174. Rotating distraction mechanism 118 raises or lowers cylindrical structure 174 within tube 170 thereby raising or lowering support structure 172 and femoral plate 130. Modular drill guide attachment 116 is configured to couple to support structure 172. In one embodiment, support structure 172 has one or more holes configured to receive one or more pegs from modular drill guide attachment 116 to retain and align femoral drill guide 110 to tensor 104. Modular drill guide attachment 116 places femoral drill guide 110 above femoral plate 130. In one embodiment, A-P adjustment couples to support structure 172. In one embodiment, A-P adjustment is screw button that can be loosened allow femoral drill guide 110 to be moved in an anterior or posterior direction to place femoral drill guide 110 near the femur to support drilling one or more holes. The screw button can be tightened when femoral drill guide 110 is in position to prevent movement during drilling.

FIG. 4B is a top view of tensor 104 in accordance with an example embodiment. Femoral plate 130 is shown extending outward from tensor 104 to support insertion into the knee joint. In one embodiment, femoral plate 130 is offset to support placing the patella to the side to insert tensor 104 and then re-placing the patella back onto the knee joint for a kinetic assessment of the knee joint. In one embodiment, load plate 120 overlies three sensors at predetermined positions. Similarly, load plate 122 overlies three sensors at predetermined positions. Electronic circuitry 176 couples the sensors underlying load plates 120 and 122 to control a measurement process and transmit measurement data to a computer. The measurement data is used to calculate a position of applied load to load plate 120 or load plate 122 or a load magnitude at the position of applied load to load plate 120 or load plate 122. As disclosed herein, the compartment height is set by rotating distraction mechanism 118 while reviewing the loading applied to plates 120 and 122. Tilt mechanism 132 is rotated to tilt femoral plate 130 relative to tibial plate 128 (not shown). In one embodiment, tilt mechanism 132 is rotated to achieve balance in the knee joint. In one embodiment, tilt mechanism 132 is a gear mechanism configured to rotate femoral plate 130. In one embodiment, tilt mechanism 132 is coupled between distraction mechanism 118 and femoral plate 130. After achieving balance, A-P adjustment is loosened and femoral drill guide 110 is positioned near the femur to drill one or more holes. In one embodiment, an equal compartment height is maintained on the medial side and the lateral side the knee joint. In one embodiment, rotation adjustment 114 is used to rotate femoral drill guide 110 to compensate for the tilt introduced by tilt mechanism 132. In one embodiment, amount of rotation of femoral drill guide 110 can be viewed on rotation adjustment 114. Alternatively, one or more sensors can be placed on tensor 104 to measure tilt of femoral plate 130 and femoral drill guide 110. The tilt of femoral plate 130 and femoral drill guide 100 would be displayed on the computer to which the measurement data is sent in real-time for review by the surgical team.

Figures 4C, 4D:
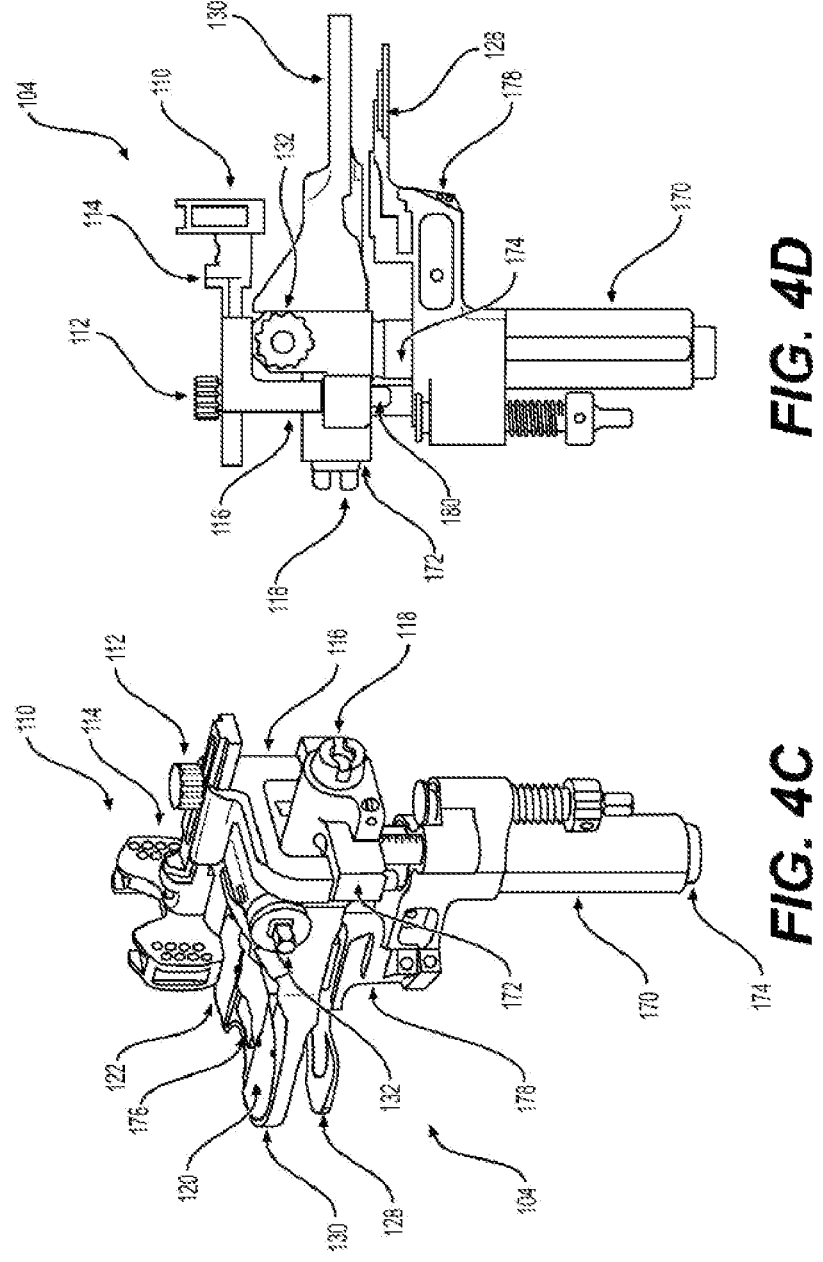

FIG. 4C is side view of tensor 104 in accordance with an example embodiment. Tensor 104 is shown with femoral plate 130 raised above tibial plate 128. A support structure 178 is coupled between tube 170 and tibial plate 128. Support structure 178 extends horizontally away from tube 170 and vertically to position tibial plate 128 below femoral plate 130. Support structure 178 is in a fixed position aligned to tube 170. Support structure 178 is configured not to flex or bend under loading when distracting the knee joint. In one embodiment, the proximal end of the tibia is cut using a PSI cutting jig 106 as shown in FIG. 1C. In one embodiment, tibial plate 128 has a planar bottom surface configured to couple to the prepared surface of the tibia. Tilt mechanism 132 is placed between femoral plate 130 and distraction mechanism 118. In one embodiment, tilt mechanism 132 comprises a gear drive configured to rotate femoral plate 130. Tilt mechanism 132 is configured to tilt femoral plate 130 medially or laterally. Tilt mechanism 132 and femoral plate 130 are raised and lowered together by distraction mechanism 118. In one embodiment, the gear drive in tilt mechanism 132 will hold position when tilted under load. Alternatively, tilt mechanism 132 can be used with a separate tilt lock to prevent movement of tilt mechanism 132 after being set. Femoral drill guide 110, rotation adjustment, 114, A-P adjustment 112, and modular drill guide attachment 116 is configured to be coupled to tensor 104 after the knee joint balance is achieved or it can be installed to tensor 104 during the balancing operation.

FIG. 4D is a side view of tensor 104 in accordance with an example embodiment. Tensor 104 is shown with femoral plate 130 being separated from tibial plate 130. Tensor 104 has compartment height corresponding to a distance between the upper surface of support structure 130 and the bottom surface of tibial plate 128. In one embodiment, the compartment height would be measured from the surface of load plate 120 or load plate 122 as shown in FIG. 4C to the bottom surface of tibial plate 128. In one embodiment, support structure 178, tibial plate 128, and tube 170 are formed as a single structure. For example, support structure 178, tibial plate 128, and tube 170 can be milled from a block of metal such as aluminum or steel. Alternatively, support structure 178, tibial plate 128, and tube 170 can be formed by other processes such as by mold or 3D printing. Support structure 178, tibial plate 128, and tube 170 are aligned to one another in predetermined positions. Support structure 178 extends tube 170 horizontally and then has a vertical component to position tibial plate 128 in a predetermined position relative to femoral plate 130.

Femoral plate 130 couples to tilt mechanism 132. Tilt mechanism 132 couples to distraction mechanism 118. Distraction mechanism 118, tilt mechanism 132, and femoral plate 130 are aligned to tibial plate 128 by cylindrical structure 174 of distraction mechanism 118. Cylindrical structure 174 fits within tube 170 and is configured to move up or down within tube 170 under control of distraction mechanism 118. Tilt mechanism 132 is configured to tilt femoral plate 130 to balance the knee joint. In one embodiment, tilt mechanism 132 can be locked after a tilt has been established by tightening a nut that is part of tilt mechanism 118 to prevent rotation of the gear mechanism. Modular drill guide attachment 116 is coupled to support structure 172 of distraction mechanism 118. Pin 180 of modular drill guide attachment 116 couples through an opening in support structure 172. Modular drill guide 116 places A-P adjustment 112, rotation adjustment 114, and femoral drill guide 110 above support structure 172, tilt mechanism 132, and femoral plate 130. Femoral drill guide 110 can be adjusted by A-P adjustment 112 and rotation adjustment 114 to drill one or more holes in the femur for pinning a femoral cutting block to cut the femur in balance at a predetermined compartment height as set by tensor 104.

Figure 5:
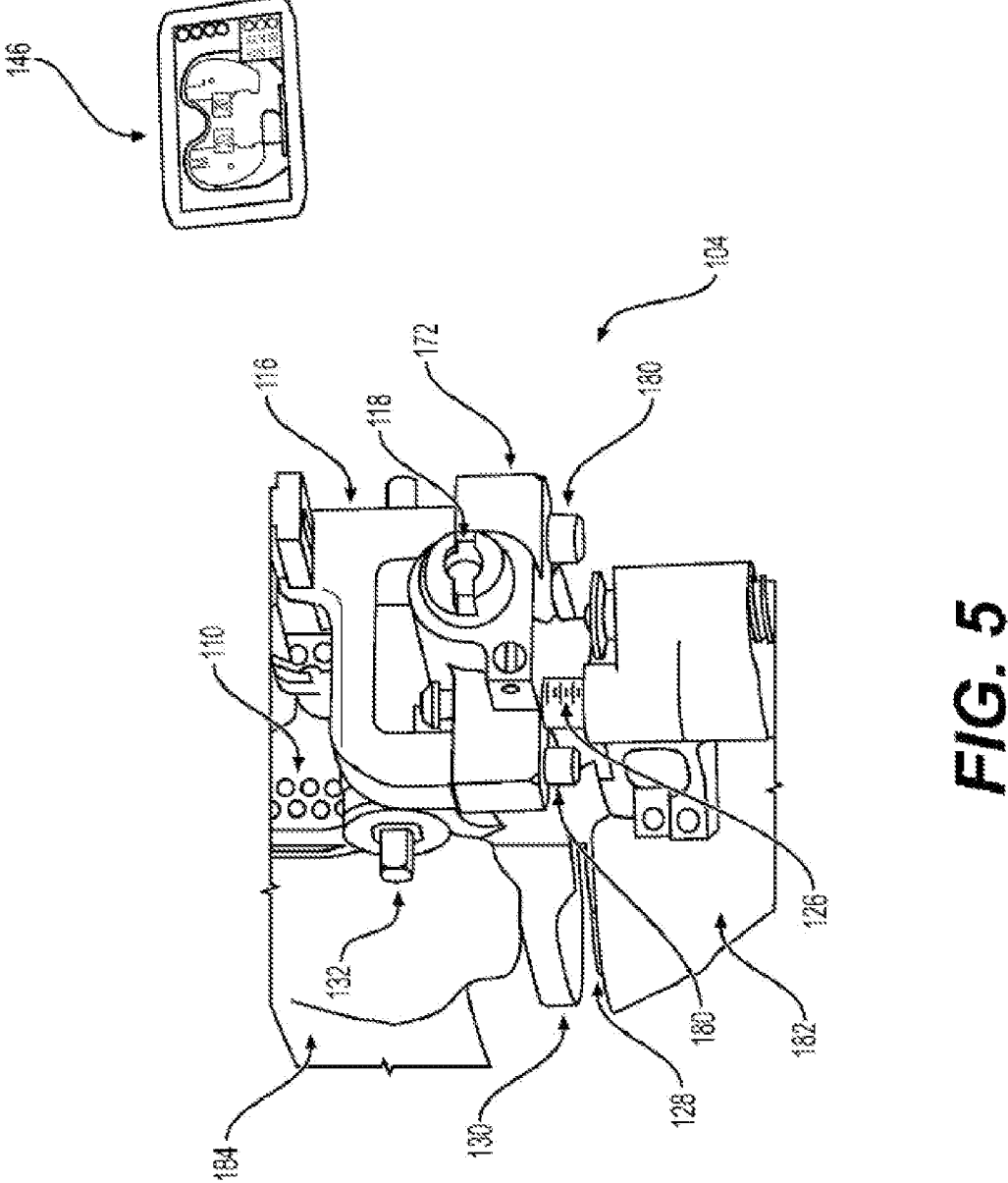
FIG. 5 illustrates a partial view of the tensor inserted in a joint.

FIG. 5 is a partial view of tensor 104 inserted in a knee joint in accordance with an example embodiment. A proximal end of tibia 182 is shown having a prepared bone surface from being cut using a PSI bone cutting guide. Tensor 104 is placed in at a minimum height and inserted in the knee joint. The minimum height of tensor 104 occurs when femoral plate 130 couples to tibial plate 128. As shown, a femur 184 is at a 90 degree angle from tibia 182. Tensor 104 can have one or more sensors configured to measure the position of femur 184 relative to tibia 182 and display the angle on computer 146 in the operating room. In the example, tensor 104 is distracted to a predetermined compartment height. The load magnitude and the position of applied load of a medial condyle and a lateral condyle coupling to femoral plate 130 are measured by tensor 104. The load magnitude and position of applied load one the medial and lateral sides of tensor 104 are shown on computer 146. The predetermined compartment height can be read from distraction gap display 126 or displayed on computer 146. The predetermined compartment height corresponds to the installation of a tibial prosthetic component, a femoral prosthetic component, and an insert. In other words, the combined thickness of the tibial prosthetic component, the femoral prosthetic component, and the insert is related to the predetermined compartment height. Tilt mechanism 132 is used to tilt femoral plate 130 to bring the knee joint in balance. In one embodiment, the predetermined compartment height is equal on the medial and lateral sides of tensor 104. In one embodiment tilt mechanism 132 brings the knee joint into balance but can make the medial compartment height differ from the lateral compartment height. Femoral drill guide 110 is rotated to correspond to the tilt produced by tilt mechanism 132 to bring the knee joint in balance. One or more holes are drilled into femur 184. The one or more holes are used to pin a PSI cutting block to femur 184. In one embodiment, the one or more holes are used to pin the PSI cutting block at an angle the produce equal compartment heights on the medial and lateral sides of the knee joint. The bone cut of femur 184 will also maintain the balance measured by tensor 104. In the example, two pins 180 of modular drill guide attachment 116 are shown inserted into support structure 172 to retain and position femoral drill guide 110 relative to femoral plate 130. The load magnitude and position of applied loading over a range of motion of the final installed prosthetic components should be approximately equal to the measurement data generated by tensor 104 that support the bone cuts in balance.

Figures 6A, 6B, 6C:
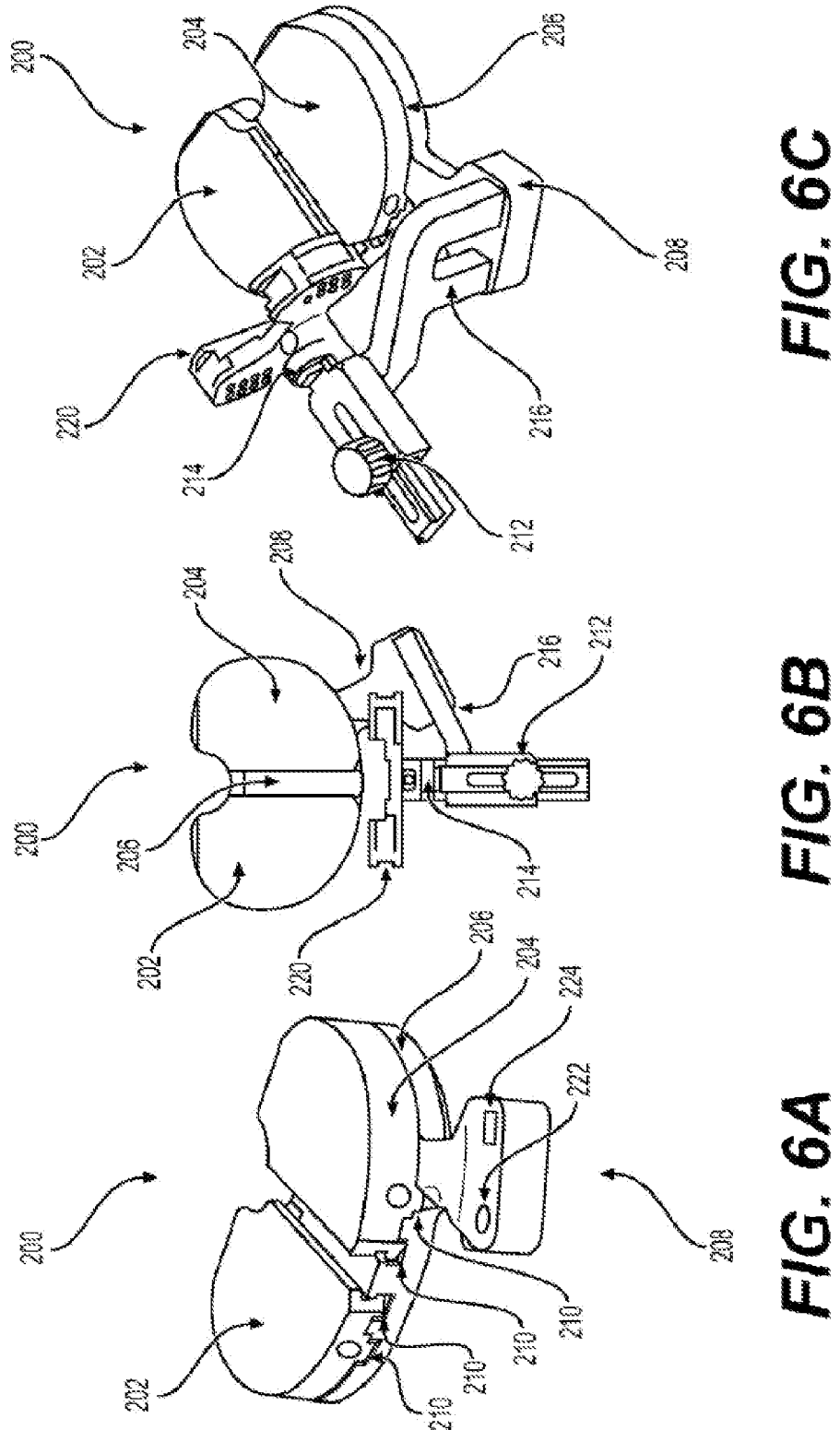
FIGS. 6A-6C illustrates an insert in accordance with an example embodiment.

FIGS. 6A-6C illustrates an insert system 200 in accordance with an example embodiment. Insert system 200 can be used in place of tensor 104 disclosed herein above to balance a knee joint and support one or more bone cuts to install one or more prosthetic components. Insert system 200 can be used with patient specific instruments (PSI) that are constructed using one or more images to form a 3D model of a femur and a tibia of the patient. In one embodiment, insert system 200 is used in conjunction with bone cutting jig 102, bone cutting jig 106, bone cutting jig 160, femoral PSI 152, or tibial PSI 154 shown in FIGS. 3A-3G. Each of the patient specific instruments are configured to couple to the femur and the tibia of the patient to cut bone using pinning holes drilled using insert system 200. In one embodiment, femoral PSI 152 is coupled to the femur to support a coronal alignment measurement. In one embodiment, tibial PSI 154 is coupled to the tibia to support the coronal alignment measurement during the balancing process using insert system 200. In one embodiment, insert system 200 is a low cost system configured to be disposable after a single use. In one embodiment, insert system 200 can be patient specific instruments based on 3D models using one or more images of the patient femur and tibia. Insert system 200 can be designed using the 3D model of the femur and tibia. Insert system 200 can be molded or manufactured using 3D print technology. In one embodiment, insert system 200 can be made of a polymer material such as polycarbonate, polyurethane, PEEK, UHMW polyurethane, or other biocompatible material. Insert system 200 can also be made from metal or metal alloy. In one embodiment, insert system 200 can be a reusable system configured to be sterilized after each use.

FIG. 6A is an illustration of an insert 206, a shim 202, and a shim 204 in accordance with an example embodiment. Insert system 200 comprises an insert 206 and a plurality of shims. The plurality of shims comprises shims for a medial side and a lateral side of insert 206. The medial side and the lateral side shims will come in different heights corresponding to final insert heights used with a final femoral prosthetic component and a final tibial prosthetic component. In one embodiment, insert system 200 will have insert 206 and a plurality of shims for a right side knee joint and an insert 206 and a plurality of shims for a left side knee joint. The insert 206 will differ for the left knee or the right knee based on the location of structure 208 extending from insert 206. The offset location of structure 208 supports the placement of a patella to the side while inserting insert system 200 or removing insert system 200 to change shims and replacing insert system 200 within the knee joint. The patella can then be placed back on the knee joint to load the knee joint over a range of motion. In one embodiment, structure 208 of insert 206 has an opening 222 and an opening 224. Openings 222 and 224 are used to couple an instrument or device to structure 208. In one embodiment, opening 222 is circular in shape. In one embodiment, opening 224 is square in shape. In one embodiment, a tool can be coupled to openings 222 and 224 having a handle to aid the surgeon in directing insert 206, shim 202, and shim 204 into the knee joint.

A shim 202 and a shim 204 are coupled to insert 206. In one embodiment, a surface of shim 202 and a surface of shim 204 are non-planar. The non-planar surface of shim 202 or shim 204 is an articular surface configured to support movement of the knee joint. Alternatively, shim 202 or shim 204 can have a planar surface. Shim 202 and shim 204 are configured to couple to insert 206. In one embodiment, insert 206 has one or more grooves 210 formed in an upper surface of insert 206. Grooves 210 are configured to support coupling shim 202 to insert 206. Similarly, insert 206 has one or more grooves 210 configured to support coupling shim 204 to insert 206. In the example, shim 202 has corresponding tongues configured to fit within grooves 210. In one embodiment, the tongues of shim 202 are aligned to grooves 210 such that shim 202 slides into insert 206 laterally. Shim 204 has corresponding tongues configured to fit within grooves 210 formed on the surface of insert 206. In one embodiment, a structural feature within grooves 210 of insert 206 will prevent further lateral movement of shim 202. Shim 202 in contact with the structural feature will place 202 in alignment with insert 206. The tongue and grooves of shim 202 and insert 206 are configured to retain shim 202 in place while supporting quick removal should a different size shim be required to achieve an appropriate balance. A structural feature is also in grooves 210 to prevent lateral movement of shim 204. In one embodiment, shim 202 and 204 can only be inserted one way such that shims for the medial side can only be placed on the medial side of insert 206 and shims for the lateral side can only be placed on the lateral side of insert 206. In the example, a shim 204 which is thicker than shim 202 was used to achieve balance within the knee joint. Note that the difference in height of shim 204 and shim 202 corresponds to a tilt as disclosed for tensor 104 of FIG. 1A. Although not shown, insert system 200 couples to a computer to receive measurement data from insert system 200. Insert system 200 includes one or more sensors coupled to electronic circuitry. The electronic circuitry controls a measurement process and transmits measurement data. The heights of shim 204 and shim 202 can be entered in the computer during the surgery and the tilt can be calculated using the heights of shim 202 and 204 stored in the computer.

FIG. 6B is a top view of insert system 200 in accordance with an example embodiment. Condyles of a femur couple to shims 202 and 204 when inserted in the knee joint. Insert system 200 includes a drill guide to support one or more bone cuts when the knee joint is in balance. In one embodiment, the drill guide is similar to the drill guide disclosed for tensor 104 in FIGS. 1A-5. Any disclosed feature or use of the drill guide for tensor 104 also applies to insert system 200. Structure 208 extends outward from insert 206. Structure 208 does not reside within the knee joint and is accessible to the surgeon when insert 206, shim 202, and shim 204 are placed in the knee joint.

Modular drill guide attachment 216 is configured to couple to structure 208 thereby placing the drill guide in proximity to the knee joint. In one embodiment, modular drill guide attachment 216 has a cylindrical pin and a square pin that are configured to fit respectively within openings 222 and 224 of structure 208. The cylindrical pin and the square pin retain modular drill guide attachment 216 to structure 208 to support drilling one or more holes in the femur. Loosening anterior-posterior (A-P) adjustment allows femoral drill guide 220 to be moved in an anterior or posterior direction. In general, femoral drill guide 220 is moved to a location that supports drilling one or more holes in the femur. A-P adjustment is then tightened to hold femoral drill guide 220 in place to prevent movement in the anterior or posterior direction. In one embodiment, the femur is cut to have equal compartment heights. Femoral drill guide 220 can be rotated using rotation adjustment 214 to angle the cut to compensate for different heights of shims 202 and 204. In one embodiment, rotation adjustment 214 has a rotation display that is visible to the surgeon or surgical team that indicates the amount of rotation. One or more holes are drilled in the femur having a predetermined rotation. A cutting block can be coupled to the femur aligned to the one or more holes thereby cutting the femur having equal compartment heights and in balance.

FIG. 6C is a side view of insert system 200 in accordance with an example embodiment. Structure 208 extends from and is offset on insert 206 to support positioning a patella to allow insert 206, shim 202, and shim 204 to be inserted in a knee joint. The patella can then be placed back on the knee joint to load the knee joint after insert 206, shim 202, and shim 204 is inserted. Structure 208 is not in the knee joint. Modular drill guide attachment 216 positions femoral drill guide 220 to be centered to the intercondylar notch. Modular drill guide attachment 216 places femoral drill guide 220 above shims 202 and 204. A-P adjustment 212 and rotation adjustment 214 are used to position femoral drill guide 220 to drill one or more holes for pinning a PSI cutting block to the femur to make a cut at a predetermined angle. In one embodiment, femoral drill guide 220 has openings for drilling holes in the medial condyle and the lateral condyle of the femur. Thus, the PSI cutting block can be attached to the femur in a manner that supports cutting femur at the predetermined angle.

Figures 7A, 7B, 7C, 7D, 7E:
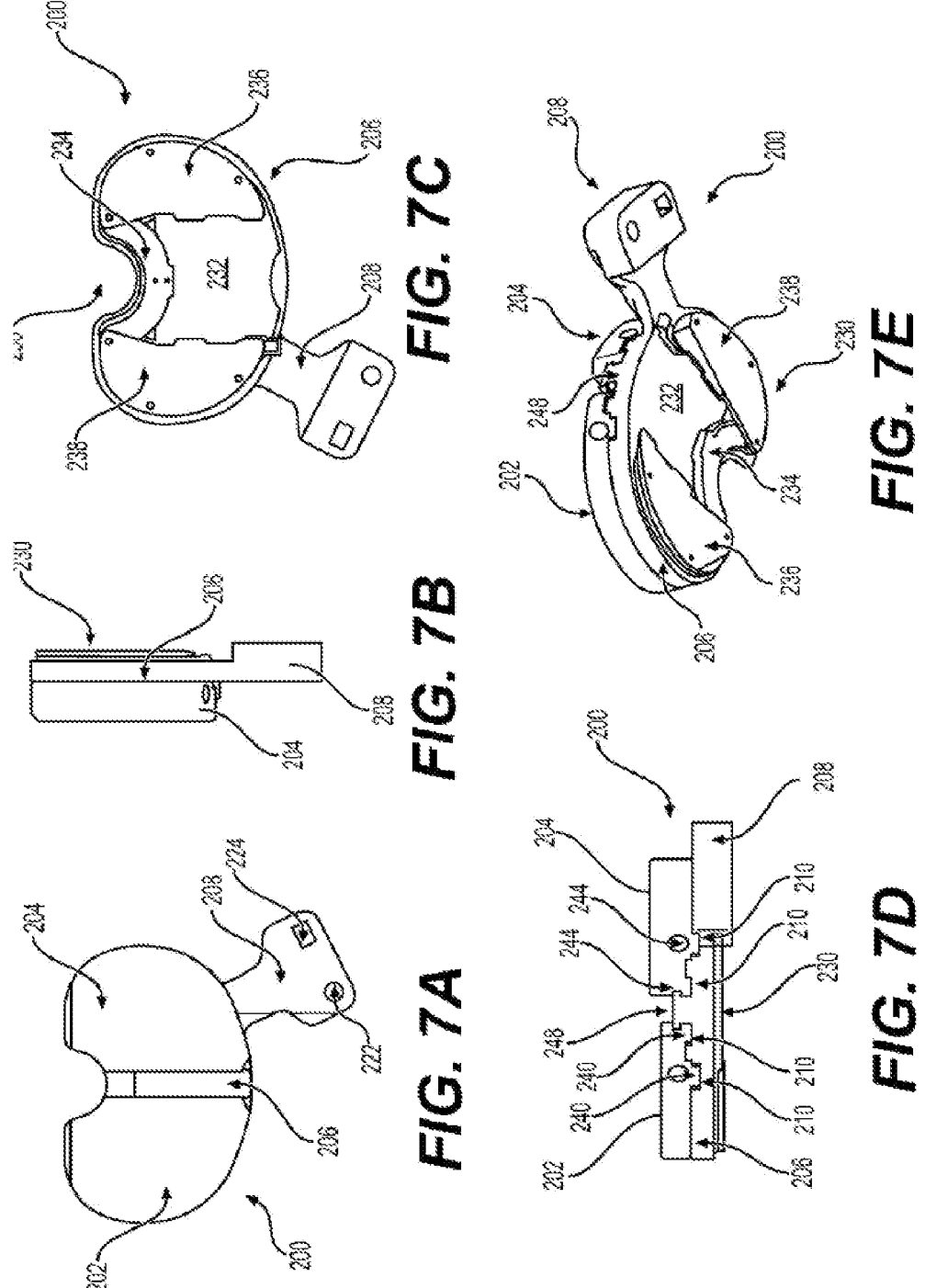
FIGS. 7A-7E illustrates the insert in accordance with an example embodiment.

FIG. 7A is a top view of insert system 200 in accordance with an example embodiment. Shim 202 and shim 204 are coupled to a top surface of insert 206. As mentioned previously, shim 202 is one of a plurality of shims each having a different height. Similarly, shim 204 is one of a plurality of shims each having a different height. In one embodiment, the plurality of shims corresponding to shim 202 are configured to couple to a first predetermined side of insert 206. In one embodiment, the plurality of shims corresponding to shim 204 are configured to couple to a second predetermined side of insert 206. In one embodiment, shim 202 will not couple to the second predetermined side of insert 206. In one embodiment, shim 204 will not couple to the first predetermined side of insert 206. Structure 208 is shown extending from insert 206. In one embodiment, structure 208 has an opening 222 and an opening 224. A tool, equipment, or device is configured to couple to openings 222 and 224. Structure 208 is configured to support, retain, and position the tool, equipment, or device relative to insert 206.

FIG. 7B is a side view of insert system 200 in accordance with an example embodiment. The side view illustrates shim 204 coupled to a top surface of insert 206. Structure 208 is shown extending from insert 206. In one embodiment, structure 208 and insert 206 are part of the same structure. For example, insert 208 and structure 208 are molded as a single structure. A sensor system 230 couples to a bottom surface of insert 206. In general, sensor system 230 comprises at least one sensor, electronic circuitry, and a power source. Sensor system 230 is configured to control a measurement process and transmit measurement data. In one embodiment, a computer receives the measurement data and displays the measurement data. The computer can include one or more software programs and is configured to process or convert the measurement data to visual, audible, or haptic forms for rapid assimilation. The computer is in the operating room for the surgeon or surgical staff to review the measurement data in real-time.

FIG. 7C is an illustration of sensor system 230 coupled to a lower surface 232 of insert 206 in accordance with an example embodiment. Sensor system 230 comprises sensors 236, sensors 238, and electronic circuitry 234. In one embodiment, sensors 236, sensors 238, and electronic circuitry 234 couple to a printed circuit board. Portions of the printed circuit board can be flexible and other portions can be rigid. The printed circuit board can have more than one layer of interconnect to couple sensors 236 and 238 to electronic circuitry 234. In one embodiment, electronic circuitry 234 includes a battery or batteries configured to power electronic circuitry 234 during the surgery. Sensor system 230 couples to a lower surface 232 of insert 206. Insert 206 can have one or more retaining features to align sensors 236, sensors 238, and electronic circuitry 234 to lower surface 232.

In one embodiment, sensors 236 underlie shim 202 and sensors 238 underlie shim 204. Electronic circuitry 234 is placed in a location that is unloaded by the musculoskeletal system when insert system 200 is inserted in the knee joint. In one embodiment, sensors 236 have load sensors placed at vertexes of a polygon. In general, this defines an area of measurement. Measurement outside the polygon can be measured but can be less accurate as some of the sensors become unloaded. Sensors 238 will have a similar arrangement as sensors 236. The area of the polygon in sensors 236 can differ from the area of sensors 238. In one embodiment, the area of measurement on the medial side of insert 206 can differ from the area of measure on the lateral side of insert 206 to support differences in contact point movement of the knee joint on the medial or lateral sides of insert 206. In one embodiment, loading applied by the musculoskeletal system to shim 202 or shim 204 is respectively coupled through sensors 236 or sensors 238. Thus, sensors 236 and sensors 238 can provide accurate measurement of the load magnitude applied to the surface of shim 202 or shim 204. The position of each sensor of sensors 236 is known relative to the articular surface of shim 202. Similarly, the position of each sensor of sensors 238 is known relative to the articular surface of shim 204. As mentioned previously, the measurement data from insert system 200 is transmitted to a computer. The computer can use the measurement data to calculate a load magnitude and a position wherein the load magnitude is applied to shim 202 or shim 204. The measurement data is used to determine balance and contact point over a range of motion of the knee joint. The computer can further identify problems that require adjustments. The computer can further provide a work flow to make the adjustments to ensure the optimization of the knee joint for performance and reliability.

FIG. 7D is an illustration of a side view of sensor system 200 in accordance with an example embodiment. Sensor system 230 is shown coupled to a bottom surface of insert 206. In one embodiment, a bottom surface of sensor system 230 extends beyond insert 206 such that the bottom surface of sensor system 230 couples to the prepared surface of the tibia when insert system 200 is inserted in the knee joint. Shim 202 and shim 204 are coupled to and aligned to the upper surface of insert 206. In the example, shim 202 has a height less than shim 204 to achieve balance in the knee joint. In one embodiment, the shim heights of shim 202 and shim 204 are provided to the computer receiving information from insert system 200. In one embodiment, the computer is computer 146 shown in FIG. 3C that is placed within the operating room for viewing by the surgeon or surgical team. Computer 146 processes information received from insert system 200 similarly to how it processes information from tensor 104 during a surgical installation. Insert system 200 provides measurement data to computer 146. Computer 146 has an interface that supports data entry such as shim height. In one embodiment, computer 146 can have a scanner for scanning code on a shim that provides information such as the height of the shim. In one embodiment, each shim of the plurality of shims can have an RF ID tag that can provide shim information to computer 146. In one embodiment, computer 146 calculates a tilt corresponding to the difference in height between shim 202 and 204. The tilt information based on shim height is used with the femoral bone cutting jig to set the compartment heights for the balanced knee joint. In one embodiment, the medial and lateral compartment heights of the knee joint are set to be equal.

Tongues 240 are formed in a bottom surface of insert 202. Grooves 210 are formed in the upper surface of insert 206. Grooves 210 are aligned to and correspond to tongues 240. Similarly, tongues 244 are formed in a bottom surface of insert 204. Grooves 246 are formed in the upper surface of insert 206. Grooves 246 are aligned to and correspond to tongues 244. A retaining feature 248 is formed as part of insert 206 between shims 202 and 204. Retaining feature 248 is configured to retain shim 202 or shim 204 to prevent shim 202 or shim 204 to disengage during a measurement process. In one embodiment, retaining feature 248 is configured to extend into a sidewall groove of shim 202 or 204. Thus, shim 202 or shim 204 can only be coupled to insert 206 by sliding shim 202 or shim 204 laterally into insert 206. Retaining feature 248 prevents shim 202 or 204 from being pressed vertically onto the top surface of insert 206. Insert 206 includes a stop that aligns shim 202 or shim 204 to insert 206 from being pushed further laterally than the stop. Removing shim 202 or shim 204 is just a reverse process of sliding out shim 202 or 204 in an opposite direction from where it was initially engaged to insert 206. Moreover, shim 202 or shim 204 cannot swap placement as only can be coupled to insert 206 as shown. In other words, shim 204 cannot replace shim 202 and vice versa.

FIG. 7E is an illustration of an angled view of insert system 200 in accordance with an example embodiment. Shim 202 and shim 204 are coupled to a top surface of insert 206. In one embodiment, shim 202 or shim 204 are coupled to insert 206 from the anterior side of insert 206. The tongues of a shim are coupled to the corresponding grooves in the top surface of insert 206 such that a bottom surface of the shim couples to the top surface of insert 206. The bottom surface of the shim slides across the top surface of insert 206 until the shim is aligned to insert 206. The retaining feature 248 also couples to the shim during the sliding process.

Structure 208 is not inserted within the knee joint and extends outward from insert 206 which is inserted in the knee joint. A tool, device, or other equipment is configured to couple to structure 208 such as a PSI bone cutting jig. As mentioned previously, insert system 200 can be a patient specific instrument created from a 3D model of the patient's leg and knee joint. A bottom view of insert system 200 illustrates sensor system 230 coupled to a lower surface 232 of insert 206. Sensor system 230 comprises sensors 236, sensors 238, and electronic circuitry 234. Electronic circuitry 234 is configured to control a measurement process and transmit measurement data to a computer such as computer 146 shown in FIG. 3C. In one embodiment, sensors 230 extends below insert 206 such that sensors 230 couples to the prepared surface of the tibia and insert 206 does not. The musculoskeletal system loading shim 202 and shim 204 transfers the load through insert 206 to sensors 236 and sensors 238. In one embodiment, sensors 236 comprise three sensors placed at vertexes of a first triangle. In one embodiment, sensors 238 comprise three sensors placed at vertexes of a second triangle. The positions of each sensor of sensors 236 and 238 is provided or known by computer 146 of FIG. 3C. The first and second triangles can differ in perimeter and area. In one embodiment, the entire loading applied to shim 202 is channeled thru the three sensors of sensors 236. In one embodiment, the entire loading applied to shim 204 is channeled thru the three sensors of sensors 238. The computer 146 of FIG. 3C receives the measurement data from sensors 236 and sensors 234. Computer 146 can calculate a position applied load to shim 202 and shim 204 and calculate the load magnitude applied at the position of applied load to shim 202 and shim 204. The measurement data supports determining a balanced condition for the knee joint.

Figures 8A, 8B:
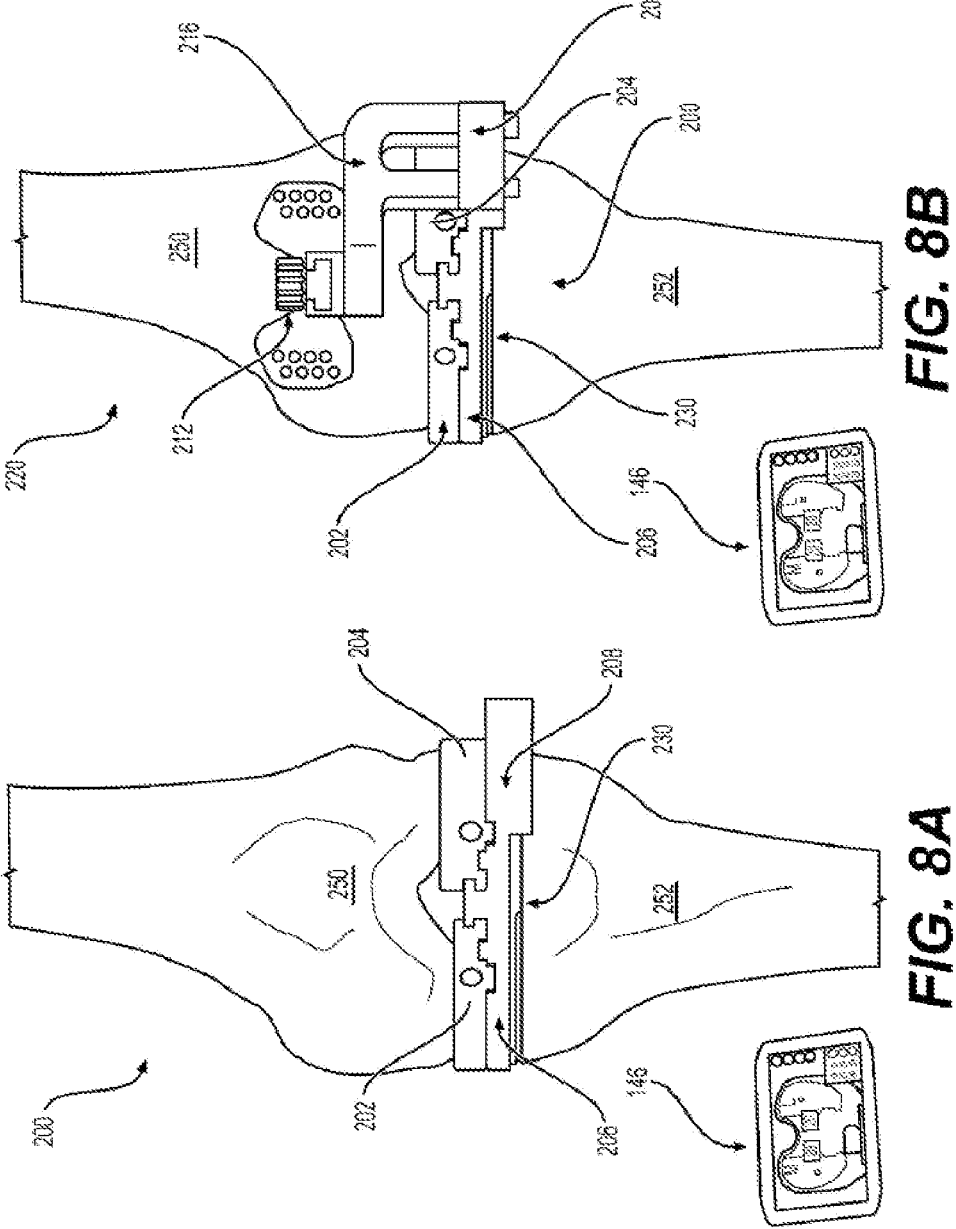
FIGS. 8A-8D illustrate steps used to perform one or more bone cuts using the insert in a knee joint in accordance with an example embodiment.

FIG. 8A is an illustration of insert system 200 in a knee joint in accordance with an example embodiment. The workflow disclosed herein below comprises one or more steps using one or more patient specific instruments and insert 206 to support installation of one or more prosthetic components. The steps can be performed in any order and no sequence is implied. Steps can be removed or replaced in the workflow depending on the application. A pre-operative plan can be put together as a guide to the surgery. The pre-operative plan can be viewed on display 146 in the operating room. In general, a surgeon or surgical team goes through a standard pre-operative planning process. In one embodiment, the pre-operative planning includes optimization of a tibial 252 or femoral location 250. In one embodiment, a PSI bone cutting jig is used to resect a proximal tibia. The bone cutting jig is a patient specific instrument PSI and a tibial resection guide. The PSI can be designed from one or more images of the femur, knee joint, and tibia. In one embodiment, a 3D model of the leg can generated from the one or more images of the femur, knee joint, and tibia. The 3D model can be used to create devices, tools, prosthesis, trialing devices, final devices or equipment designed specifically for the patient surgery. In one embodiment, a 3D printer can be used to manufacture the devices, tools, prosthesis, trialing devices, final devices or equipment. In a first step, a PSI bone cutting jig is coupled to tibia 252. The PSI bone cutting jig is used to cut the proximal end of tibia 252 in a manner that supports alignment to the leg mechanical axis.

In a second step, medial and lateral forces are balanced in the knee joint. In general the leg is positioned in flexion greater than 5 degrees and less than 80 degrees. In one embodiment, the leg is positioned at approximately 10 degrees of flexion with insert system 200 inserted in the knee joint. Sensor system 230 couples to the prepared surface of tibia 252 cut in the first step. Condyles of femur 250 couple to shim 202 and shim 204 to support movement of the knee joint. In one embodiment, the forces on the medial and lateral sides of the knee joint by the medial condyle and lateral condyle of femur 250 are balanced by selecting different heights for shims 202 and 204. In general, the pre-planning may include determining an approximate compartment height for the knee joint. The pre-planned compartment height can be trialed in the knee joint. Sensor system 200 can be removed from the knee joint if the measured balanced as viewed on computer 146 is non-optimal. A shim or both shims are removed and a new shim or shims can be installed on insert 206 to adjust the balance, load value, and contact points. A new shim having reduced thickness will lower the load magnitude applied by the corresponding condyle of the femur to insert system 200. Conversely, a new shim having increased thickness will increase the load magnitude applied by the corresponding condyle of the femur to insert system 200. The load magnitude and the contact point location on the new shim can be viewed in real-time on computer 146. The surgeon has the options of re-cutting the tibia or soft tissue tensioning to further optimize the balance of the knee joint or correct for defects not identified during pre-planning.

In a third step, the heights of the medial shim and the lateral shim have been selected. The heights of the medial shim and the lateral shim are entered in computer 146 and computer 146 calculates the tilt. The knee joint is then moved from 10 degrees flexion to full limb extension. Ideally, the limb can be placed in full extension. Additional steps can be performed to optimize the knee if the knee joint hyperextends when placed in full extension or the knee does not extend to full extension. For example, in one embodiment, one or more sensors within insert 176 transmit measurement data to a computer having a display. In one embodiment, the computer is in the operating room providing the measurement data in real-time to the surgeon and surgical team for making adjustments or confirming that measurements are within specification. In a step 192, drill guide 116 is coupled to insert 176 and one or more holes are drilled. A femoral bone cutting jig is pinned to the femur. The femoral bone cutting jig is a patient specific instrument. The femur is than resected using the femoral bone cutting jig. In a step 194, the leg is balanced in flexion. In one embodiment, the leg is flexed to approximately 90 degrees with insert 176 in the knee joint. In one embodiment, the balance forces are based on patient specific forces determined when the leg was placed in extension in a prior step. Measurement data is displayed on the computer in real-time. In a step 196, drill guide 116 is coupled to insert 176. One or more holes are drilled with the femur in flexion using drill guide 116. The drill guide 116 is then removed from insert 176. A femoral cutting jig is then pinned to the femur in flexion. The femoral cutting jig is a patient specific instrument. The resection depths can be confirmed prior to a cut being made. The femoral cuts are then performed to the femur in flexion. The tibial prosthetic component, femoral prosthetic component, and the insert can then be installed to complete the prosthetic knee surgery.

FIG. 8B is an illustration of drilling one or more holes in femur 250 to support a bone cut to femur 250 in accordance with an example embodiment. Patient specific instruments enable all implant and instrument sizing to be pre-determined, minimizes reusables, and is a patient kitted disposable system. Predictively balancing the knee joint at the native femoral step enables intraoperative efficiency by preventing the need for any re-cuts or adjustments. A patient specific instrumentation surgical plan could be displayed on computer 146 for reference throughout the surgery. The workflow is a significant advance compared to other patient specific instrument products. The system enables intraoperative flexibility that is not possible with patient specific instrument products alone. In one embodiment, the system disclosed herein can be adapted for use with a surgical robot.

In a fourth step, a drill guide is coupled to structure 208 extending from insert 208. In one embodiment, the drill guide can be a patient specific instrument (PSI) manufactured specifically for drilling femur 250 of the patient based on one or more images of femur 250, tibia 252, and the knee joint. In one embodiment, a 3D model of the patient femur 250, tibia 252, and the knee joint is used to define the drill guide. The drill guide comprises a modular drill guide attachment 216, an anterior-posterior (A-P) adjustment 212, a rotation adjustment 214 (not shown), and femoral drill guide 220. In one embodiment, modular drill guide attachment 216 has two pegs configured to couple to two openings in structure 208 of insert 206. Modular drill guide attachment 216 is a support structure that is retained to insert 206 and positions femoral drill guide 220 in a location to drill one or more holes in an anterior portion of the condyles of femur 250. In one embodiment, structure 208 is offset relative to femur 250, modular drill guide attachment 216 places femoral drill guide 220 centered to the intercondylar notch. In one embodiment, femoral drill guide 220 has a medial side and a lateral side template for drilling holes to the anterior side of the condyles of femur 250. A-P adjustment 212 can be used to position femoral drill guide 220 near femur 250. A-P adjustment 212 is tightened to hold the A-P position of femoral drill guide 220. Femoral drill guide 220 can be rotated to change where the holes are drilled on femur 250 on the medial and lateral condyle. In one embodiment, the medial and lateral compartment heights of the knee joint are determined to be equal for the installation of the femoral prosthetic component. Note that shims 202 and 204 result in unequal heights (tilt) due to their height differences. Rotation adjustment 212 is rotated to compensate for the tilt introduced by shims 202 and 204 such that the medial and lateral compartment heights of the knee joint are equal while maintain the balance as disclosed in steps 2 and 3. The tilt of the one or more holes drilled in femur 250 will "tilt" the PSI cutting jig such that the bone cut yields equal compartment heights at the measured balance. In one embodiment, adjustments can be made prior drilling one or more holes into the distal end of the femur. In one embodiment, adjustments such as a bone cut, soft tissue tensioning, or rotation of insert system 200 can be performed to change the balance, contact point location on shims 260 and 264, or load magnitudes applied to shims 260 and 264 with the knee joint in flexion. Computer 146 can display measurement data such as load magnitudes, position of applied load, or contact point rotation (of insert system 200) in real-time to support the adjustments in real-time. The adjustments are made to optimize, improve fit, reliability, and performance of the knee joint.

In a fifth step, insert system 200 is removed from the knee joint after drilling one or more holes into the medial and lateral condyles of femur 250. A PSI bone cutting jig is coupled to the distal end of femur 250. The patient specific cutting jig is configured to fit femur 250 based on the 3D model disclosed herein above. In one embodiment, pins are used to hold the PSI cutting jig to femur 250. The location of the pins will tilt the patient specific cutting jig when pinned to femur 250. The PSI cutting jig will have a slot for receiving a bone saw. The bone saw will cut distal end of the femur corresponding to the tilt introduced in step 4 by rotation adjustment 212 to femoral drill guide 220. In one embodiment, the bone cut to the distal end of femur yields equal medial and lateral compartment heights in the knee joint at the balance measured by sensor system 230.

Figures 8C, 8D:
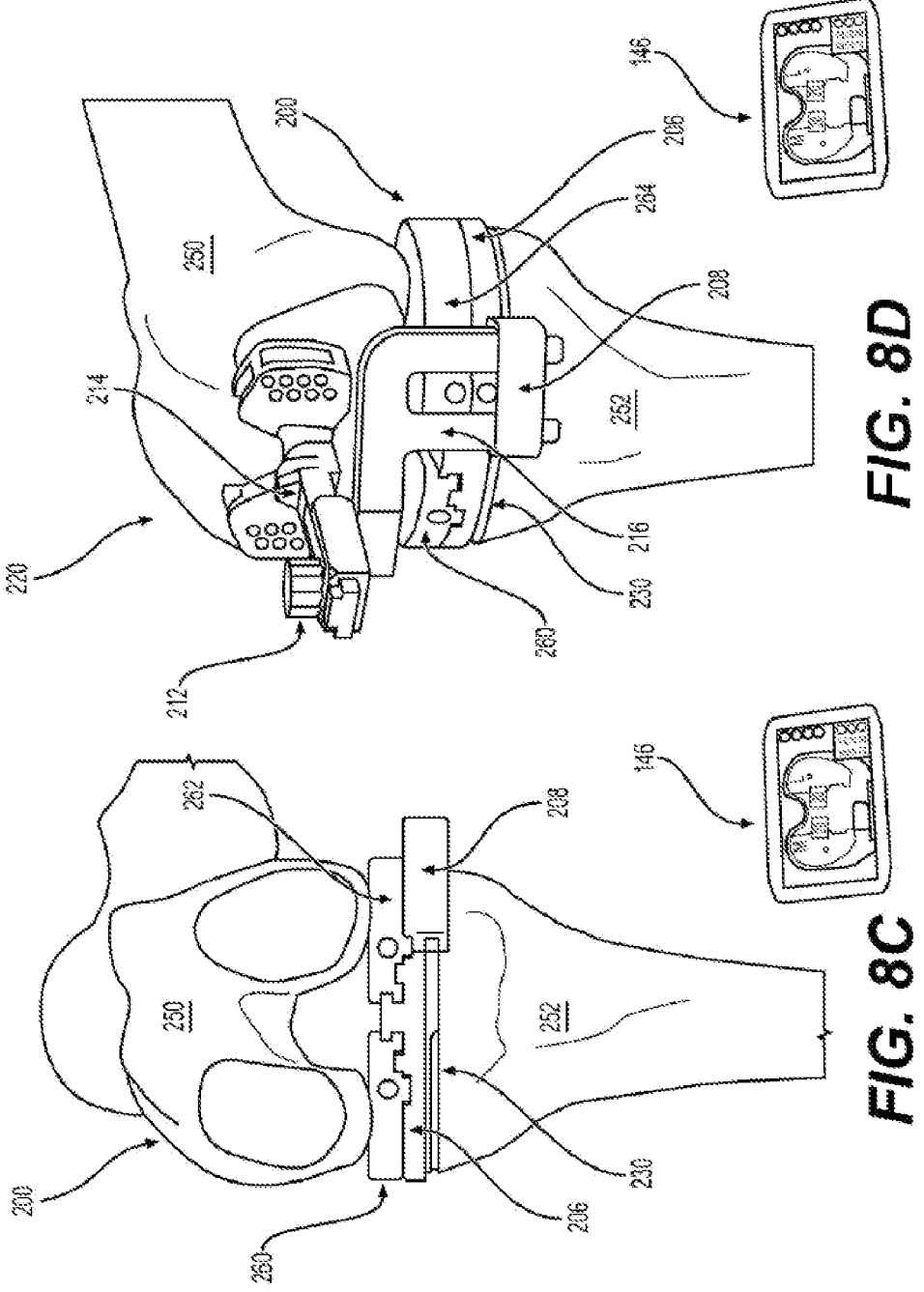

FIG. 8C illustrates the knee in flexion with insert system 200 within the knee joint in accordance with an example embodiment. In general, the leg can be placed in flexion at greater than 45 degrees but less than 135 degrees. In one embodiment, the leg is placed in flexion at 90 degrees. In one embodiment, the knee joint is balanced based on specific forces determined previously when the leg was in extension. In other words, the balance of the leg at 90 degrees in flexion is made to approximately the balance in extension. In one embodiment, the compartment height of the knee joint with the leg at 90 degrees flexion is made to match the compartment height with the leg in extension. Shims 260 and 262 are installed to insert 206 to trial the knee joint at 90 degrees flexion. In the example embodiment, the selection of shims 260 and 262 set the compartment height equal to the final compartment height with the knee joint in extension. Insert system 200 is placed in the knee joint such that sensor system 230 couples to the prepared surface of tibia 252. A posterior portion of the condyles of femur 250 couple to shims 260 and 262. Note that the posterior portion of the condyles of femur 250 that couple to shims 260 and 262 are uncut. The force or load applied by the condyles of femur 250 to insert system 200 are monitored on computer 206. The contact points of the medial and lateral condyles to shim 260 and 262 are also displayed on computer 146. Typically, the loading on shim 260 and 262 are not in balance for the equal compartment heights. Ideally, the loading on at least one of shims 260 or 262 will be approximately equal to the loading when the leg is in extension or measures a higher loading. In a sixth step, insert system 200 is inserted in the knee joint with the leg in flexion at 90 degrees and the measurement data is viewed on computer 146 to determine what is required to balance the knee joint at 90 degrees flexion. In the example, the side measuring equal to or higher loading than what was measured when the knee joint was in extension is identified. In the example, the loading on the remaining side measures low compared to what was measured when the knee joint was in extension. Insert system 200 is removed and a shim of increased height replaces the shim that measured low loading. Insert system 200 is then inserted in the knee joint at 90 degrees flexion. In one embodiment, both compartments measured with the knee joint at 90 degrees flexion now measure loading equal to or greater than the loading measured with the knee joint in extension.

FIG. 8D is an illustration of drilling one or more holes in the condyles of femur when the knee joint is in flexion in accordance with an example embodiment. In the sixth step disclosed herein above the knee joint is balanced in flexion. In the example, shim 260 and shim 264 are selected to balance the knee joint when placed in flexion at 90 degrees. In one embodiment, the compartment height within the knee joint at 90 degrees flexion is selected to be substantially equal to the compartment height selected when the knee joint was in in extension as disclosed in FIG. 8A. In one embodiment, 260 and shim 262 is selected to have the same height as shim 202. In fact, shim 260 can be shim 202 that is reused when insert system 200 is inserted into the knee joint at 90 degrees flexion. In the example, shims 260 and 264 were selected to balance the knee joint and determine the compartment height in the sixth step.

In a seventh step, shims 260 and 264 have been selected to determine balance and compartment height of the knee joint in 90 degrees flexion. In one embodiment, adjustments can be made prior drilling one or more holes into the distal end of the femur. Adjustments such as a bone cut, soft tissue tensioning, or rotation of insert system 200 can be performed to optimize the balance, contact point location on shims 260 and 264, or change load magnitudes applied to shims 260 and 264 with the knee joint in flexion. Computer 146 can display measurement data such as load magnitudes, position of applied load, or contact point rotation (of insert system 200) in real-time to support the adjustments in real-time. The adjustments are made to optimize, improve fit, reliability, and performance of the knee joint. The drill guide is coupled to structure 208 extending from insert system 200 after the adjustments are made. In one embodiment, the drill guide can be a patient specific instrument (PSI) manufactured specifically for drilling femur 250 of the patient based on one or more images of femur 250, tibia 252, and the knee joint. In one embodiment, a 3D model of the patient femur 250, tibia 252, and the knee joint is used to define the drill guide. The drill guide comprises a modular drill guide attachment 216, an anterior-posterior (A-P) adjustment 212, a rotation adjustment 214 (not shown), and femoral drill guide 220. Although shown as the same drill guide as used in FIG. 8B, the drill guide can also be a PSI drill guide made specifically for drilling into the distal end of femur 250. In one embodiment, modular drill guide attachment 216 has two pegs configured to couple to two openings in structure 208 of insert 206. Modular drill guide attachment 216 is a support structure that is retained to insert 206 and positions femoral drill guide 220 in a location to drill one or more holes in the prepared surface of femur 250 as disclosed in the fifth step on the medial condyle or the lateral condyle of femur 250. In one embodiment, structure 208 is offset relative to femur 250, modular drill guide attachment 216 places femoral drill guide 220 centered to the intercondylar notch. In one embodiment, femoral drill guide 220 has a medial side and a lateral side template for drilling holes to a distal end of femur 250 on the medial condyle and the lateral condyle. A-P adjustment 212 can be used to position femoral drill guide 220 near femur 250. A-P adjustment 212 is tightened to hold the A-P position of femoral drill guide 220. Femoral drill guide 220 can be rotated to change where the holes are drilled on femur 250 on the medial and lateral condyle. In one embodiment, the medial and lateral compartment heights of the knee joint in 90 degrees flexion are determined to be equal for the installation of the femoral prosthetic component. In the example, the compartment height of the knee joint in 90 degrees flexion is made to be equal to the compartment height of the knee joint in extension as disclosed herein above. Note that shims 260 and 264 result in unequal heights (tilt) due to their height differences. Rotation adjustment 214 is rotated to compensate for the tilt introduced by shims 260 and 264 such that the medial and lateral compartment heights of the knee joint are equal while maintain the balance as disclosed set with the knee joint in 90 degrees flexion. The tilt of the one or more holes drilled in femur 250 will "tilt" the PSI bone cutting jig such that the bone cut yields equal compartment heights at the measured balance.

In an eighth step, insert system 200 is removed from the knee joint. A PSI bone cutting jig is coupled to the femur. In one embodiment, the PSI bone cutting jig is pinned to femur 250 using the one or more holes drilled in the seventh step to align the PSI bone cutting jig to cut the femur for equal compartment heights and in balance as set in the sixth step with the knee joint at 90 degrees flexion. The PSI bone cutting jig will have a slot for receiving the bone saw. The bone saw will a posterior portion of the condyles of femur 250 corresponding to the tilt introduced in step 7 by rotation adjustment 212 to femoral drill guide 220. In one embodiment, the bone cut to the distal end of femur yields equal medial and lateral compartment heights in the knee joint at the balance measured by sensor system 230. In a ninth step, the final femoral prosthetic component is installed after a posterior portion of the condyles have been removed with the support of the PSI bone cutting jig. The final femoral component is configured to couple to a distal end of femur 250 having the compartment heights disclosed herein above for the knee joint in extension and the knee joint in 90 degrees flexion. The final tibial prosthetic component is coupled to the proximal end of tibia 252. A final insert is then coupled to the final tibial prosthetic component and the wound due to the surgery is sealed.

Discussed herein below is a surgical orthopedic system configured for use in an operating room. The surgical orthopedic system is configured to support an installation of one or more prosthetic components in a manner that decreases surgical time while improving performance and reliability. Components from FIGS. 1A-8D will be identified and described. The surgical orthopedic system comprises one or more patient specific instruments. In one embodiment, a surgeon and surgical team prepare a pre-operative plan for the patient. The pre-operative plan can include the design and manufacture of one or more patient specific instruments. The pre-operative plan can be provided to computer 146 and displayed on the display coupled to computer 146 in the operating room. In one embodiment, the pre-operative plan supports the optimization of a tibial or femoral location. Patient specific instruments are designed specific to the patient taking into account the size and shape of the musculoskeletal system. The design of patient specific instruments can use one or more images of the musculoskeletal system. In one embodiment, a 3D model of the musculoskeletal system can be created from the one or more images to support the design of a patient specific instrument. In the example, bone cutting jigs 102, 106, and 160 are patient specific instruments configured to support one or more bone cuts of a patient's femur or tibia. Similarly, insert system 200 comprising insert 206, shim 202, shim 204, and the drill guide can be patient specific instruments configured to couple to the patient's femur or tibia. In general, a plurality of medial and lateral shims are provided each having different heights for a medial side and a lateral side optimization of the balance to insert system 200.

Tensor 104 comprises a distraction mechanism 118 and a tilting mechanism 132. In general, tensor 104 has a moving structure that moves and tilts relative to a fixed structure. The fixed structure comprises tibial plate 128, support structure 178, and tube 170. The fixed structure of tensor 104 does not move. Distraction mechanism 118 moves femoral plate 130 relative to tibial plate 128. In one embodiment, distraction mechanism 118 comprises a gear drive that when rotated will raise or lower femoral support 130. In one embodiment, distraction mechanism 118 includes a cylindrical structure 174 that couples within tube 170. Cylindrical structure 174 can have a side having gear teeth that couples to the gear drive of distraction mechanism 118. In one embodiment, raising and lowering of femoral plate 130 is aligned to tube 170 via cylindrical structure 174. Tilt mechanism 132 couples between femoral plate 130 and distraction mechanism 118. Tilt mechanisms 132 is configured to tilt femoral plate 130 thereby changing a medial and lateral compartment height to support balancing the knee joint. In one embodiment, tilt mechanism 132 is a gear drive coupled to femoral plate 130 whereby rotating tilt mechanism 132 rotates femoral plate 130. Tensor 104 is inserted in the knee joint such that femoral plate 130 and tibial plate 128 respectively couple to the condyles of the femur and the proximal end of the tibia. Tensor 104 is configured to support balancing the knee joint. In one embodiment, the knee joint is balanced with the leg in flexion greater than 5 degrees and less than 80 degrees. A drill guide is configured to couple to tensor 104 to drill one or more holes in a bone to support attaching bone cutting jig for preparing a bone surface for a prosthetic component in balance.

Load plates 120 and 122 are configured to couple to condyles of the femur. Underlying load plates 120 and 122 are a sensor system. A plurality of sensors underlie plate 120 and a plurality of sensors underlie plate 122. Electronic circuitry 176 couples to the plurality of sensors underlying plates 120 and 122. The electronic circuitry 176 controls a measurement process and transmits measurement data to a computer 146. The plurality of sensors underlying load plate 120 and 122 are at predetermined locations and are configured to measure the load applied to load plates 120 or 122 at the predetermined locations. Computer 146 receives the measurement data from electronic circuitry 176 and can calculate a position of applied load on load plate 120 or load plate 122 and the load magnitude at the position of applied load. Computer 146 uses the predetermined locations and the measured load at the predetermined locations to calculate the load magnitude and position of applied load. Measurement data is displayed on a display of computer 146 in real-time within the operating room for the surgeon and surgical team to view. Sensor system 230 disclosed in FIGS. 7A-7E corresponds to the sensor system used in tensor 104 to measure load and position of load. The description of sensor system 230 also applies to the sensor system in tensor 104.

A bone cutting jig 106 is configured to couple to a bone of the patient. In one embodiment, the bone cutting jig is a PSI tibial resection guide. In one embodiment, cutting jig 106 supports a resection of a proximal tibia of the patient's leg. After resection of the tibia the leg is placed in flexion. As mentioned previously, the leg is placed in flexion greater than 5 degrees but less than 80 degrees. In one embodiment, the leg is placed in flexion at approximately 10 degrees. Tensor 104 is placed in the knee joint with the leg in flexion at 10 degrees. Tensor 104 is configured under surgeon control to balance the knee joint.

The leg is moved to extension after the surgeon sets the balance. In one embodiment, the balance set by tensor 104 with the leg in extension will correspond to a compartment height. The measured compartment height corresponds to the combined thickness of the prosthetic components when placed in the knee joint. The prosthetic components will have the same balance as measured by tensor 104 when installed in the knee joint. The drill guide is coupled to tensor 104. The drill guide comprises modular drill guide attachment 116, anterior-posterior (A-P) adjustment 112, rotation adjustment 114, and femoral drill guide 110. In one embodiment, drill guide 110 is configured to drill one or more holes in a medial condyle and a lateral condyle of the femur. Modular drill guide attachment 116 couples and positions A-P adjustment 112, rotation adjustment 114, and femoral drill guide 110 to the distal end of the femur. The A-P adjustment 112 allows precise positioning of femoral drill guide 110 to the distal end of the femur. The one or more holes drilled into the femur are drilled in an anterior portion of the medial and lateral condyles. In general, the compartment heights on the medial and lateral sides created by tensor 104 will not be equal in height when the knee joint is set in balance. In one embodiment, the prosthetic components are designed to have equal compartment heights on the medial and lateral sides. Thus, femoral drill guide 110 is rotated using rotation adjustment 114 by an amount corresponding to the tilt of femoral plate 130. The plurality of holes are drilled having the tilt introduced by rotation adjustment 114. Tensor 104 is removed from the knee joint. The one or more holes drilled in the femur are used to couple bone cutting jig 106 to the femur in alignment to have a bone cut with the leg in extension such that the knee joint has equal compartment heights in the balance set by tensor 104. In one embodiment, bone cutting jig 106 is a PSI distal femoral guide. The PSI distal femoral guide is pinned to the femur having the tilt introduced by rotating femoral drill guide 110. The PSI distal femoral guide has a guide slot for a bone saw to resect the distal end of the femur having equal compartment height and in the balance set by tensor 104.

In one embodiment, the leg may not be able to be moved to extension after the leg is placed in balance at 10 degrees flexion. The knee joint is assessed by the surgeon or surgical team and one or more adjustments are made to the knee joints. The one or more adjustments can be a bone cut, tissue tensioning, rotation of tensor 104 or other adjustment that increases the range of motion of the leg. The adjustment is deemed correct if the leg can be placed in extension. The knee joint is also assessed by the surgeon or surgical team if the knee joint hyperextends when placing the knee joint or leg in extension. One or more adjustments are made to prevent hyperextension. The one or more adjustment that decreases the range of motion of the leg can be a bone cut, tissue tensioning, rotation of tensor 104 or other adjustments that reduce the range of motion of the leg near extension. The adjustment is deemed correct if the leg can be placed in extension and does not hyper extend.

The leg is placed in flexion at approximately 90 degrees after the resection of the distal end of the femur. Tensor 104 is configured to be inserted back into the knee joint. Tensor 104 is used to balance the knee joint with the leg in flexion at 90 degrees. In one embodiment, the compartment height with the leg in flexion at 90 degrees is made to be equal to the compartment height with the leg in extension. In one embodiment, the balance of the knee joint in flexion at 90 degrees is made to be equal to the balance of the knee joint in extension. The drill guide is coupled to tensor 104 and one or more holes are drilled into the femur. In one embodiment, the one or more holes are drilled in the prepared surface of the distal end of the femur corresponding to the medial and lateral condyles. In general, femoral plate 130 will have a tilt when tensor 104 sets the knee joint in balance with the leg in flexion at 90 degrees. In the example, the compartment height set by tensor 104 will also be set to same compartment height when the leg was in extension. Femoral drill guide 110 is rotated using rotation adjustment 114 to a tilt corresponding to femoral plate 130 to yield equal compartment height at the balance set by tensor 104. One or more holes are drilled in the prepared surface of the distal end of the femur with the leg position at 90 degrees flexion. Tensor 104 is then removed from the knee joint. A bone cutting jig 160 is configured to couple to the femur. In one embodiment, bone cutting jig 160 is a PSI femoral resection guide that is pinned to the femur using the one or more holes that were drilled in the femur of the leg when placed in flexion at 90 degrees. In one embodiment, the one or more holes used to couple the PSI femoral resection guide impose a tilt on the PSI femoral resection guide to cut the posterior portion of the medial and lateral condyles to have equal compartment heights in the balance set by tensor 104. In the example, the balance and the compartment height will be equal in 90 degrees flexion and in extension. The femur is resected using bone cutting jig 160. Bone cutting jig 160 is removed and the final tibial component, insert, and final femoral component are installed. In one embodiment, the compartment height of final tibial component, insert, and final femoral component when installed in the knee joint will be equal to the compartment height set by tensor 104 with the leg at degrees flexion and in extension.

A surgical insert system 200 is disclosed herein to support the installation of one or more prosthetic components. In one embodiment, surgical insert system 200 is configured to support at least one bone cut of the musculoskeletal system. Surgical insert system 200 called herein after as insert system 200 is used with a pre-operative plan. The pre-operative plan is provided to computer 146 coupled to insert system 200 and displayed for viewing by the surgeon and surgical team. In one embodiment, one or more images are taken of the musculoskeletal system during pre-operative planning. In one embodiment, the one or more images of the musculoskeletal system can be used to form a 3D image or 3D model of joint or bone requiring surgery. In one embodiment, the 3D image, or 3D model is used to support a manufacture of one or more patient specific instruments (PSI) configured to be used in the surgery in support of the installation of one or more prosthetic components. In one embodiment, the PSI can be bone cutting jigs to cut a femur or a tibia. In one embodiment, the PSI can be insert system 200 configured to fit the patient musculoskeletal system. In the example, surgical insert system 200 is configured to be used in a knee joint. Surgical insert system 200 can be adapted for use in different joints such as spine, hip, shoulder, elbow, wrist, ankle, fingers, toes, or the musculoskeletal system. The surgical insert system 200 comprises one or more patient specific instruments (102, 106, 152, 154, and 160), an insert 206, a plurality of medial shims, a plurality of lateral shims, and a sensor system 230. Insert 206 has an upper surface and a lower surface. A structure 208 extends from insert 206 and is configured to position and retain at least one tool, equipment, device, or component. In one embodiment, structure 208 is offset to one side of insert 206. The offset is configured to support placing a patella to the side, inserting insert system 200 in the knee joint, and replacing the patella back on the knee joint. The patella will load the knee joint thereby supporting a kinetic assessment of the knee joint. In one embodiment, a drill guide is configured to couple to structure 208. The drill guide is configured to support drilling one or more holes to align a bone cutting jig to a femur. A medial shim, a lateral shim, insert 206, and the sensor system are configured to be placed in the knee joint. In one embodiment, structure 208 extends outside the knee joint.

A selected lateral shim 202 and a selected medial shim 204 are respectively chosen from the plurality of lateral shims and the plurality of medial shims. Selected lateral shim 202 and selected medial shim 204 will be called shim 202 and shim 204 or lateral shim 202 and medial shim 204 herein after. In one embodiment, each shim of the plurality of medial shims has a different height. Similarly, each shim of the plurality of lateral shims has a different height. In one embodiment, lateral shim 202 and medial shim 204 are selected based on the pre-operative plan and the one or more images. Lateral shim 202 and medial shim 204 are configured to couple to an upper surface of insert 206. In one embodiment, the upper surface of insert 206 includes retaining features to hold and align lateral shim 202 and medial shim 204 to insert 206. In one embodiment, a medial shim can only be coupled to a medial side of the upper surface of insert 206. Similarly, a lateral shim can only be couple to a lateral side of the upper surface of insert 206.

Sensor system 230 is configured to couple to a lower surface of insert 206. Sensor system 230 includes one or more sensors configured to measure one or more parameters as disclosed herein above. In one embodiment, sensor system 230 comprises sensors 236 and sensors 238 respectively configured to measure loading applied to a medial side or a lateral side of insert system 200 by a medial condyle or a lateral condyle of the femur. Sensors 236 and sensors 238 couple to electronic circuitry 234. Electronic circuitry 234 is configured to control a measurement process and transmit measurement data to computer 146. The measurement data can be provided on the display of computer 146 in real-time. Sensor system 230 can include one or more printed circuit boards that can be flexible or rigid to interconnect sensors 236, sensors 238, and components of electronic circuitry 234 to form sensor system 230. In one embodiment, sensors 236, sensors 238, and electronic circuitry 234 are encapsulated to be hermetically sealed. In one embodiment, sensors 236 or sensors 238 comprise three sensors located at vertexes of a triangle at known predetermined locations. The known predetermined locations of sensors 236 or sensors 238 are provided to computer 146 to perform calculations related to position of applied load and load magnitude at the position of applied load. Measurement data from each of the three sensors of sensors 236 or the three sensors of sensors 238 are provided to computer 146. In one embodiment, loading applied by the medial condyle or the lateral condyle of the femur to shim 204 or shim 202 is respectively coupled to the three sensors of sensors 238 or sensors 236. In one embodiment, sensor system 230 couples to the lower surface 232 of insert 206. Loading applied to shim 202 or shim 204 by the femur couples through insert 206 to sensors 236 and 238. In one embodiment, a lower surface of sensors 236 and 238 extends below insert 206 to couple to the prepared surface of the tibia when insert system 200 is inserted in the knee joint.

A shim height of shim 202 and a shim height of shim 204 are provided to computer 146 prior to generating measurement data. Bone cutting jig 102 is coupled to the tibia. In one embodiment, bone cutting jig 102 is a PSI tibial resection guide. The PSI tibial resection guide is coupled to the tibia according to the pre-operative plan. A bone saw is guided by PSI tibial resection guide to resect the proximal tibia. Insert system 200 is inserted into the knee joint and enabled to start transmitting measurement data to computer 146. In general, the leg is placed in flexion between 5 degrees and 80 degrees. In one embodiment, the leg is placed in flexion at 10 degrees. In one embodiment, computer 146 uses the predetermined locations of sensors 236 and 238 and the measurement data to calculate the position applied load to shim 202 or shim 204 and the load magnitude at the position of applied load to shim 202 or shim 204 in real-time. The display of computer 146 can display the contact point to shim 202 or shim 204 and the corresponding load magnitude at the contact point on shim 202 or shim 204. Computer 146 will also calculate the tilt corresponding to a difference in height between shims 202 and 204. The surgeon determines what the desired load magnitude is on the medial and lateral sides that achieve the balance for the knee joint. In one embodiment, the load magnitudes can be determined during the pre-operative planning. Alternatively, the surgeon can determine the appropriate load magnitudes on the medial and lateral sides of the knee joint by movement of the leg with insert system 200 installed. The surgeon then can use the quantitative measurement data on the display to determine if the knee joint is in balance and the tilt corresponding to the balance. Insert system 200 can be removed from the knee joint if it is determined that the balance is incorrect or needs to be adjusted. Medial shim 204, lateral shim 202, or both can be replaced with another shim from the plurality of medial shims or the plurality of lateral shims. In one embodiment, only the plurality of medial shims will couple to the medial side of insert 206. Similarly, only the plurality of lateral shims will couple to the lateral side of insert 206. After changing at least one of the medial or lateral shims insert system 200 is then replaced in the knee joint to determine if the knee joint balance is acceptable to the surgeon. The process can be continued until a satisfactory result is achieved. In one embodiment, the surgeon can further adjust the balance of the knee joint by a bone cut, soft tissue tensioning, insert rotation, or other method. In one embodiment, electronic circuitry 230 includes a sensor configured to measure rotation of insert 206 from a reference position. The amount of rotation of insert 206 from the reference position is displayed on the display of computer 146. In one embodiment, femoral PSI 152 is coupled to the femur to support a coronal alignment measurement. In one embodiment, tibial PSI 154 is coupled to the tibia to support the coronal alignment measurement during the balancing process using insert system 200.

The leg is placed in extension after achieving the balance at 10 degrees flexion. The knee joint is configured to be reassessed and one or more adjustments made to increase a range of motion if the leg cannot be placed in extension. The adjustment can comprise a bone cut, soft tissue tensioning, rotating insert 206, or other adjustment that increases a range of motion of the leg to extension. The knee joint is configured to be reassessed and one or more adjustments made to decrease a range of motion if the leg hyperextends when placed in extension. A drill guide is coupled to structure 208. The drill guide comprises a modular drill guide attachment 216, an anterior-posterior (A-P) adjustment 212, a rotation adjustment 214, and femoral drill guide 110. The drill guide is coupled to structure 208 of insert 206. The knee joint is in balance and the leg is in extension. The measurement data from sensor system 230 can include leg position sensing. The position (e.g. extension) can be displayed on the display of computer 146. One or more drill holes are drilled in the femur of the leg using femoral drill guide 110. Insert system 200 is removed from the leg in extension after drilling the holes. In one embodiment, the medial compartment height is made to be equal to the lateral compartment height. Obviously, if shim 202 differs in height from shim 204 to achieve balance the compartment heights are different. The height difference between shim 202 and shim 204 corresponds to a tilt that is calculated on computer 146. The tilt of shim 202 and 204 can be negated by using rotation adjustment 214 to rotate femoral drill guide 220 to compensate for the tilt thereby yielding equal medial and lateral compartment heights after cutting the femur. The one or more drill holes are used to couple bone cutting jig 106 to the femur. In one embodiment, pins are inserted through bone cutting jig 106 into the one or more drill holes in the femur. In one embodiment bone cutting jig 106 is a PSI distal femoral guide. The PSI distal femoral guide is configured to couple to the femur and support resection of the femur. Bone cutting jig 106 is coupled to the femur having a tilt that produces a bone cut on the femur having equal compartment heights when the leg is in extension and in balance as previously measured by insert system 200.

The leg is then placed in flexion at 90 degrees. Insert system 200 is placed in the knee joint. In one embodiment, the initial compartment height of insert system 200 with the leg in flexion at 90 degrees is made equal to the compartment height set with the leg in extension. In the example, lateral shim 260 and medial shim 264 are selected to be used in insert system 200 with the leg in flexion at 90 degrees. In one embodiment, the balance with the leg in flexion at 90 degrees is made to be the same when the balance was set with the leg in extension. In general, insert system 200 is removed from the leg in flexion at 90 degrees and reinserted with one or more different shims until the knee joint is in balance at the same compartment height set with the leg in extension. In one embodiment, the surgeon can further adjust the balance of the knee joint by a bone cut, soft tissue tensioning, insert rotation, or other method. The drill guide is then coupled to structure 208 of insert 206 with the leg in flexion at 90 degrees. One or more drill holes are drilled into the femur with the leg in flexion at 90 degrees. Similarly to the leg in extension, the medial shim and the lateral shim will not be the same height. In the example, the selection and use of lateral shim 260 and medial shim 264 results in insert system 200 being in balance with the leg in flexion at 90 degrees. The medial and lateral shim heights with the leg in balance are provided to computer 146. Computer 146 displays the tilt corresponding to the medial and lateral shim heights with the leg in flexion at 90 degrees. The tilt of lateral shim 260 and medial shim 264 can be negated by using rotation adjustment 214 to rotate femoral drill guide 220 to compensate for the tilt thereby yielding equal medial and lateral compartment heights with the leg in flexion at 90 degrees after cutting the femur. As mentioned previously, the medial and lateral compartment heights of the leg in flexion at 90 degrees will equal the medial and lateral compartment heights with the leg in extension. Also, the balance in flexion at 90 degrees will be equal to the balance with the leg in extension. Insert system 200 is removed from the knee joint with the leg in flexion at 90 degrees. The one or more drill holes in the femur drilled when the leg was in flexion at 90 degrees are used to couple bone cutting jig 160 to the femur. In one embodiment, pins are inserted through bone cutting jig 160 into the one or more drill holes made in the femur with the leg in flexion at 90 degrees. In one embodiment bone cutting jig 160 is a PSI femoral guide. The PSI femoral guide is configured to couple to the femur and support resection of the femur. Bone cutting jig 160 is coupled to the femur having a tilt that produces a bone cut on the femur having equal compartment heights when the leg is in flexion at 90 degrees and in balance as previously measured by insert system 200 with the leg in flexion at 90 degrees. The femur with the leg in flexion at 90 degrees is resected. Bone cutting jig 160 can be removed. The final tibial prosthetic component, an insert, and a final femoral prosthetic component are installed in the knee joint. The result is a knee joint in balance with the compartment heights of the leg in extension equal to the compartment heights in flexion at 90 degrees.

It should be noted that very little data exists on implanted orthopedic devices. Most of the data is empirically obtained by analyzing orthopedic devices that have been used in a human subject or simulated use. Wear patterns, material issues, and failure mechanisms are studied. Although, information can be garnered through this type of study it does yield substantive data about the initial installation, post-operative use, and long term use from a measurement perspective. Just as each person is different, each device installation is different having variations in initial loading, balance, and alignment. Having measured data and using the data to install an orthopedic device will greatly increase the consistency of the implant procedure thereby reducing rework and maximizing the life of the device. In at least one exemplary embodiment, the measured data can be collected to a database where it can be stored and analyzed. For example, once a relevant sample of the measured data is collected, it can be used to define optimal initial measured settings, geometries, and alignments for maximizing the life and usability of an implanted orthopedic device.

The present invention is applicable to a wide range of medical and nonmedical applications including, but not limited to, frequency compensation; control of, or alarms for, physical systems; or monitoring or measuring physical parameters of interest. The level of accuracy and repeatability attainable in a highly compact sensing module or device may be applicable to many medical applications monitoring or measuring physiological parameters throughout the human body including, not limited to, bone density, movement, viscosity, and pressure of various fluids, localized temperature, etc. with applications in the vascular, lymph, respiratory, digestive system, muscles, bones, and joints, other soft tissue areas, and interstitial fluids.

While the present invention has been described with reference to particular embodiments, those skilled in the art will recognize that many changes may be made thereto without departing from the spirit and scope of the present invention. Each of these embodiments and obvious variations thereof is contemplated as falling within the spirit and scope of the invention.

The invention claimed is:

1. A method for evaluating a knee joint using a tensor, the method comprising steps of:
    moving the knee joint to a flexion position;
    placing a tensor in the knee joint;
    distracting the knee joint to a first gap using a distraction mechanism of the tensor;
    measuring at least a first load value indicating a knee joint tension using a sensor;
    displaying the first load value on a computer;
    moving the distracted knee joint to a maximum extension position, and
    determining whether the knee joint in the maximum extension position is in a full extension position of the knee joint,
    wherein the tensor includes a tilting mechanism, a first femoral plate and a second femoral plate.

2. A method according to claim 1, wherein if the knee joint hyperextends or does not achieve full extension in the maximum extension position, distracting the knee joint to adjust the first gap to a second gap different from the first gap and moving the distracted knee joint to the maximum extension position to determine whether the knee joint is in the full extension position.

3. A method according to claim 2, wherein if the knee joint in the maximum extension position is in a full extension position of the knee joint, moving the knee joint to a maximum flexion position and determining whether the knee joint in the maximum flexion position is equal to a flexion position of at least 90 degrees.

4. A method according to claim 3, wherein if the knee joint in the maximum flexion position is less than 90 degrees, distracting the knee joint to adjust the first gap to a second gap different from the first gap and moving the knee joint to the maximum flexion position to determine whether the knee joint in the maximum flexion position is equal to the flexion position of at least 90 degrees.

5. A method according to claim 1, wherein if the knee joint hyperextends or does not achieve full extension in the maximum extension position, adjusting the knee joint tension by soft tissue tensioning to a second load value different from the first load value and moving the distracted knee joint to the maximum extension position to determine whether the knee joint is in the full extension position.

6. A method according to claim 5, wherein if the knee joint in the maximum extension position is in a full extension position of the knee joint, moving the knee joint to a maximum flexion position and determining whether the knee joint in the maximum flexion position is equal to a flexion position of at least 90 degrees.

7. A method according to claim 6, wherein if the knee joint in the maximum flexion position is less than 90 degrees, adjusting the knee joint tension by soft tissue tensioning and moving the knee joint to the maximum flexion position to determine whether the knee joint in the maximum flexion position is equal to the flexion position of at least 90 degrees.

8. A method according to claim 1, wherein the step of moving the knee joint to a flexion position includes a step of moving the knee joint to a 10 degrees flexion position.

9. A method according to claim 1, wherein the step of distracting the knee joint includes a step of balancing the knee joint by tilting the first femoral plate of the tensor such that the first load value on the first femoral plate is equal to a second load value on the second femoral plate.

10. A method for evaluating a knee joint using a tensor, the method comprising steps of:
    moving the knee joint to a first position;
    placing a tensor in the knee joint;
    distracting the knee joint to a first gap using a distraction mechanism of the tensor;
    measuring a first load value indicating a knee joint tension using a sensor;
    moving the distracted knee joint to a maximum extension position, and
    determining whether the knee joint in the maximum extension position is in a full extension position of the knee joint,
    wherein if the knee joint hyperextends in the maximum extension position, distracting the knee joint to adjust the first gap to a second gap different from the first gap and moving the distracted knee joint to the maximum extension position to determine whether the knee joint is in the full extension position.

11. A method according to claim 10, wherein if the knee joint does not achieve full extension in the maximum extension position, distracting the knee joint to adjust the first gap to a second gap different from the first gap and moving the distracted knee joint to the maximum extension position to determine whether the knee joint is in the full extension position.

12. A method according to claim 10, wherein if the knee joint in the maximum extension position is in a full extension position of the knee joint, moving the distracted knee joint to a maximum flexion position and determining whether the knee joint in the maximum flexion position is equal to a flexion position of at least 90 degrees.

13. A method according to claim 12, wherein if the knee joint in the maximum flexion position is less than 90 degrees, distracting the knee joint to adjust the first gap to a second gap different from the first gap and moving the distracted knee joint to the maximum flexion position to determine whether the knee joint in the maximum flexion position is equal to the flexion position of at least 90 degrees.

14. A method according to claim 10, wherein if the knee joint hyperextends in the maximum extension position, adjusting the knee joint tension by soft tissue tensioning to a second load value different from the first load value and moving the distracted knee joint to the maximum extension position to determine whether the knee joint is in the full extension position.

15. A method according to claim 10, wherein if the knee joint does not achieve full extension in the maximum extension position, adjusting the knee joint tension by soft tissue tensioning to a second load value different from the first load value and moving the distracted knee joint to the maximum extension position to determine whether the knee joint is in the full extension position.

16. A method according to claim 15, wherein if the knee joint in the maximum extension position is in a full extension position of the knee joint, moving the distracted knee joint to a maximum flexion position and determining whether the knee joint in the maximum flexion position is equal to a flexion position of at least 90 degrees.

17. A method according to claim 15, wherein if the knee joint in the maximum flexion position is less than 90 degrees, adjusting the knee joint tension by soft tissue tensioning and moving the distracted knee joint to the maximum flexion position to determine whether the knee joint in the maximum flexion position is equal to the flexion position of at least 90 degrees.

18. A method according to claim 10, wherein the step of moving the knee joint to the first position includes a step of moving the knee joint to a 10 degrees flexion position.

* * * * *